(12) United States Patent
Keaney et al.

(10) Patent No.: US 9,481,669 B2
(45) Date of Patent: Nov. 1, 2016

(54) PLADIENOLIDE PYRIDINE COMPOUNDS AND METHODS OF USE

(71) Applicant: Eisai R&D Management Co., Ltd., Tokyo (JP)

(72) Inventors: Gregg F. Keaney, Lexington, MA (US); John Wang, Andover, MA (US); Baudouin Gerard, Belmont, MA (US); Kenzo Arai, Tsukubamirai (JP); Xiang Liu, Winchester, MA (US); Guo Zhu Zheng, Lexington, MA (US); Kazunobu Kira, Ushiku (JP); Parcharee Tivitmahaisoon, Boston, MA (US); Sudeep Prajapati, Somerville, MA (US); Nicholas C. Gearhart, Durango, CO (US); Yoshihiko Kotake, Tsuchirua (JP); Satoshi Nagao, Tsukuba (JP); Regina Mikie Kanada Sonobe, Nagareyama (JP); Masayuki Miyano, Tsukubamirai (JP); Norio Murai, Tsukuba (JP); Silvia Buonamici, Boston, MA (US); Lihua Yu, Acton, MA (US); Eunice Sun Park, Arlington, MA (US); Betty Chan, Harvard, MA (US); Peter G. Smith, Arlington, MA (US); Michael P. Thomas, Stoneham, MA (US); Ermira Pazolli, Wayland, MA (US); Kian Huat Lim, Burlington, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 14/710,687

(22) Filed: May 13, 2015

(65) Prior Publication Data

US 2015/0329528 A1 Nov. 19, 2015

Related U.S. Application Data

(60) Provisional application No. 61/993,423, filed on May 15, 2014.

(51) Int. Cl.
*C07D 405/06* (2006.01)
*C07D 405/14* (2006.01)
*A61K 31/496* (2006.01)

(52) U.S. Cl.
CPC ........... *C07D 405/14* (2013.01); *C07D 405/06* (2013.01)

(58) Field of Classification Search
None
See application file for complete search history.

(56) References Cited

U.S. PATENT DOCUMENTS

| 7,026,352 B1 | 4/2006 | Mizui et al. |
| 2005/0245514 A1 | 11/2005 | Kotake et al. |
| 2006/0009439 A1 | 1/2006 | Kotake et al. |
| 2006/0079572 A1 | 4/2006 | Mizui et al. |
| 2006/0141589 A1 | 6/2006 | Okuda et al. |
| 2006/0235002 A1 | 10/2006 | Nagai et al. |
| 2007/0199741 A1 | 8/2007 | Noumi |
| 2008/0070286 A1 | 3/2008 | Machida et al. |
| 2008/0112956 A1 | 5/2008 | Nakamura et al. |
| 2008/0312317 A1 | 12/2008 | Miyano et al. |

FOREIGN PATENT DOCUMENTS

| EP | 1380579 A1 | 1/2004 |
| EP | 2136209 A1 | 12/2009 |
| EP | 2 145 886 A1 | 1/2010 |
| WO | WO 2008/126918 A1 | 10/2008 |

OTHER PUBLICATIONS

Wang et al. New England Journal of Medicine, vol. 365;26 Dec. 2011.*
Cancer Drug Design and Discovery, Neidle, Stephen,ed. (Elsevier/Academic Press), pp. 427-431 (2008).*
International Search Report and Written Opinion, PCT/US2015/030464, mailed Jul. 21, 2015.
Darman, R.B. et al. (Nov. 3, 2015) "Cancer-Associated SF3B1 Hotspot Mutations Induce Cryptic 30 Splice Site Selection through Use of a Different Branch Point" *Cell Rep*, 13(5):1033-1045.
David, C.J. and Manley, J.L. (2010) "Alternative pre-mRNA splicing regulation in cancer: pathways and programs unhinged" *Genes Dev*, 24:2343-2364.
Dvinge, H. et al. (2016) "RNA splicing factors as oncoproteins and tumour suppressors" *Nat Rev Cancer*, 16(7):413-430.
H3 Biomedicine Inc. (May 11, 2016) Press release: "Biomedicine Receives FDA Acceptance for Investigational New Drug Application Novel Hematologic Compound Bolsters Company's Emerging Drug Pipeline" [online]. Retrieved from: https://www.h3biomedicine.com/2016/05/11/biomedicine-receives-fda-acceptance-for-investigational-new-drug-application-novel-hematologic-compound-bolsters-companys-emerging-drug-pipeline/; on Aug. 8, 2016 (3 pages).

(Continued)

*Primary Examiner* — Emily Bernhardt
(74) *Attorney, Agent, or Firm* — Finnegan, Henderson, Farabow, Garrett & Dunner LLP

(57) ABSTRACT

The present invention provides novel pladienolide pyridine compounds, pharmaceutical compositions containing such compounds, and methods for using the compounds as therapeutic agents. These compounds may be useful in the treatment of cancer, particularly cancers in which agents that target the spliceosome and mutations therein are known to be useful.

46 Claims, 6 Drawing Sheets

(56) References Cited

OTHER PUBLICATIONS

Hong, D.S. et al. (2014) "A phase I, open-label, single-arm, dose-escalation study of E7107, a precursor messenger ribonucleic acid (pre-mRNA) spliceosome inhibitor administered intravenously on days 1 and 8 every 21 days to patients with solid tumors" *Invest New Drugs*, 32:436-444.
Kim, E. et al. (May 11, 2015) "SRSF2 Mutations Contribute to Myelodysplasia by Mutant-Specific Effects on Exon Recognition" *Cancer Cell*, 27(5):617-630.
Madan, V. et al. (2015) "Aberrant splicing of U12-type introns is the hallmark of ZRSR2 mutant myelodysplastic syndrome" *Nat. Commun*, 6:6042 doi: 10.1038/ncomms7042. HHS Public Access Author Manuscript; available in PMC Jul. 14, 2015 [online]. Retrieved from: http://www.ncbi.nlm.nih.gov/pmc/articles/PMC4349895/ (32 pages).
Shirai, C.L. et al. (May 11, 2015) "Mutant U2AF1 Expression Alters Hematopoiesis and Pre-mRNA Splicing In Vivo" *Cancer Cell*, 27(5):631-643.
Voskoglou-Nomikos, T. et al. (Sep. 15, 2003) "Clinical Predictive Value of the in Vitro Cell Line, Human Xenograft, and Mouse Allograft Preclinical Cancer Models" *Clin Cancer Res*, 9(11):4227-4239.
Yoshida, K. and S. Ogawa (2014) "Splicing factor mutations and cancer" *WIREs RNA*, 5:445-459.
Biankin AV et al. Pancreatic cancer genomes reveal aberrations in axon guidance pathway genes. Nature. Nov. 15, 2012; 491(7424): 399-405.
Catalogue of somatic mutations in cancer (COSMIC). Cosmic gene overview: SF3B1. Wellcome Trust Sanger Institute, Genome Research Limited. 1 p, downloaded May 1, 2015. http://cancer.sanger.ac.uk/cosmic/gene/overview?ln=SF3B1.
Damm F et al. SFB1 mutations in myelodysplastic syndromes: clinical associations and prognostic implications. Leukemia. 2012; 26: 1137-1140.
Deboever C et al. Transcriptome sequencing reveals potential mechanism of cryptic 3' splice site selection in SF3B1-mutated cancers. PLOS Computational Biology. Mar. 13, 2015; DOI:10.1371/journal.pcbi.1004105: 1/19.
Ellis MJ et al. Whole-genome analysis informs breast cancer response to aromatase inhibition. Nature. Jun. 21, 2012; 486: 383-360.
Eskens F Alm et al. Phase 1 pharmacokinetic and pharmacodynamic study of the first-in-class spliceosome inhibitor E7107 in patients with advanced solid tumors. Cancer Therapy: Clinical. Nov. 15, 2013; 19(22): 6296-304.
Furney SJ et al. SF3B1 mutations are associated with alternative splicing in uveal melanoma. Cancer Discovery. Oct. 2013; 3(10): 1122-9.
Je EM et al. Mutational analysis of splicing machinery genes SF3B1, U2AF1 and SRSF2 in myelodysplasia and other common tumors. International Journal of Cancer. Feb. 5, 2013; 133: 260-266.
Kanada RM et al. Total synthesis of the potent antitumor macrolides pladienolide B and D. Angew. Chem. Int. Ed. 2007; 46: 4350-4355.
Kar SA et al. Spliceosomal gene mutations are frequent events in the diverse mutational spectrum of chronic myelomonocytic leukemia but largely absent in juvenile myelomonocytic leukemia. Haematologica. Jan. 2013; 98: 107-117.
Kotake Y et al. Splicing factor SF3b as a target of the antitumor natural product pladienolide. Nature Chemical Biology. Sep. 2007; 3(9): 570-575.
Maciejewski JP and Padgett RA. Defects in spliceosomal machinery: a new pathway of leukaemogenesis. British Journal of Haemotology. 2012; 158: 165-173.
Maguire SL et al. SF3B1 mutations constitute a novel therapeutic target in breast cancer. Journal of Pathology. 2015; 235: 571-580.
Makishima H et al. Mutations in the spliceosome machinery, a novel and ubiquitous pathway in leukemogenesis. Apr. 5, 2012; 119(14): 3203-3210.
Malcovati L et al. Clinical significance of SFB1 mutations in myelodysplastic syndromes and myelodysplastic/myeloproliferative neoplasms. Blood. Dec. 8, 2011; 118(24): 6239-6246.
Papaemmanuil E et al. Somatic SFB1 mutation in myelodysplasic with ring sideroblasts. The New England Journal of Medicine. Oct. 13, 2011; 365(15): 1384-1395.
Quesada V et al. Exome sequencing identifies recurrent mutations of the splicing factor SFB1 gene in chronic lymphocytic leukemia. Nature Genetics. Jan. 2012; 44(1): 47-52.
Rossi D et al. Mutations of the SF3B1 splicing factor in chronic lymphocytic leukemia: association with progression and fludarabine-refractoriness. Blood. Dec. 22, 2011; 118(26): 6904-6908.
Sakai T et al. Pladienolides, new substances from culture of *Streptomyces platensis* MER-11107. I. Physico-chemical properties and structure elucidation. The Journal of Antibiotics. Mar. 2004; 57(3): 173-179.
Sakai T et al. Pladienolides, new substances from culture of *Streptomyces platensis* MER-11107. II. Physico-chemical properties and structure elucidation. The Journal of Antibiotics. Mar. 2004; 57(3): 180-187.
Scarlett CH et al. Pancreatic cancer genomes reveal aberrations in axon guidance pathway genes. Nature. Nov. 15, 2012; 491: 399-405.
Scott LM and Rebel VI. Acquired mutations that affect pre-mRNA splicing in hematologic malignancies and solid tumors. J Natl Cancer Inst. Oct. 16, 2013; 105(20): 1540-1549.
Tefferi A and Vardiman JW. Myeloplastic syndomes. New England Journal of Medicine. Nov. 5, 2009; 361(19): 1872-85.
Yokoi A et al. Biological validation that SF3b is a target of the antitumor macrolide pladienolide. FEBS Journal. 2011; 278; 4870-4880.
Yoshida K et al. Frequent pathway mutations of splicing machinery in myelodysplasia. Nature. Oct. 2011; 478: 64-69.

\* cited by examiner

PLADIENOLIDE PYRIDINE COMPOUNDS AND METHODS OF USE

BACKGROUND

The present invention provides novel organic compounds and pharmaceutical compositions containing such compounds. These compounds may be useful in the treatment of cancer, particularly cancers in which agents that target the spliceosome and mutations therein are known to be useful.

In eukaryote organisms, newly synthesized messenger RNAs typically have multiple introns, which are excised to provide the mature mRNA. The spliceosome is a multisubunit complex that accomplishes this task. The spliceosome consists of five small nuclear RNAs (snRNAs; U1-6) in combination with a variety of proteins. Mutations in spliceosome genes have been found in various types of cancers.

For example, mutations in the splicing factor 3B subunit 1 (SF3B1) of the spliceosome exist in a number of cancers and comprise a target for anticancer agents. Such cancers include, but are not limited to, myelodysplastic syndrome (MDS), leukemia such as chronic lymphocytic leukemia (CLL), chronic myelomonocytic leukemia (CMML), and acute myeloid leukemia (AML), and solid tumors such as breast cancer and uveal melanoma.

Compounds isolated from the bacteria *Streptomyces platensis* (Sakai, Takashi; Sameshima, Tomohiro; Matsufuji, Motoko; Kawamura, Naoto; Dobashi, Kazuyuki; Mizui, Yoshiharu. Pladienolides, New Substances from Culture of *Streptomyces platensis* Mer-11107. I. Taxonomy, Fermentation, Isolation and Screening. *The Journal of Antibiotics*. 2004, Vol. 57, No. 3.), termed pladienolides and discovered while screening for inhibitors of the vascular endothelial growth factor (VEGF) promoter, inhibit expression of a reporter gene controlled by human VEGF promoter, which inhibition is known to be a useful mechanism of action for anticancer agents.

These compounds also inhibit proliferation of U251 human glioma cells in vitro. The most potent of these compounds, Pladienolide B, inhibits VEGF-promoted gene expression with an $IC_{50}$ of 1.8 nM, and inhibits glioma cell proliferation with an $IC_{50}$ of 3.5 nM. The structure of pladienolide B is known, (Sakai, Takashi; Sameshima, Tomohiro; Matsufuji, Motoko; Kawamura, Naoto; Dobashi, Kazuyuki; Mizui, Yoshiharu. Pladienolides, New Substances from Culture of *Streptomyces platensis* Mer-11107. II. Physico-chemical Properties and Structure Elucidation. *The Journal of Antibiotics*. Vol. 57, No. 3. (2004)) and pladienolide B is known to target the SF3b spliceosome to inhibit splicing and alter the pattern of gene expression (Kotake et al., "Splicing factor SF3b as a target of the antitumor natural product pladienolide", Nature Chemical Biology 2007, 3, 570-575).

Certain pladienolide B compounds, as well as other pladienolide compounds, are likewise known, as disclosed the following patent applications: WO 2002/060890; WO 2004/011459; WO 2004/011661; WO 2004/050890; WO 2005/052152; WO 2006/009276; and WO 2008/126918. For example, a pladienolide compound, (8E,12E,14E)-7-((4-Cycloheptylpiperazin-1-yl)carbonyl)oxy-3,6,16,21-tetrahydroxy-6,10,12,16,20-pentamethyl-18,19-epoxytricosa-8,12,14-trien-11-olide, also known as E7107, is a semisynthetic derivative of the natural product pladienolide D, and the results of its Phase I study have been reported.

However, additional agents useful in the treatment of cancer, particularly cancers in which agents that target the spliceosome and mutations therein are known to be useful, are needed.

SUMMARY OF THE INVENTION

The purpose of the present invention is to provide a compound of formula 1 ("Compound 1"), a compound of formula 2 ("Compound 2"), a compound of formula 3 ("Compound 3"), and a compound of formula 4 ("Compound 4"):

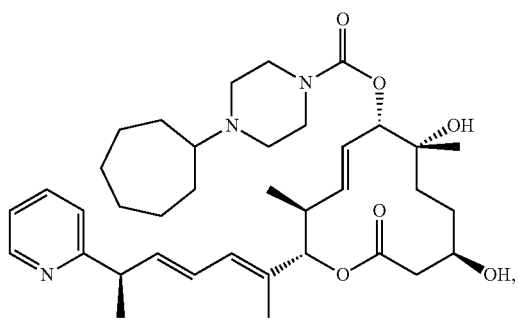

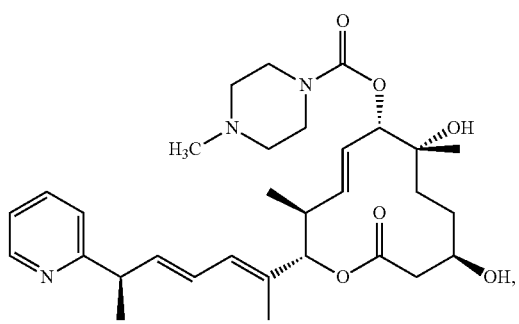

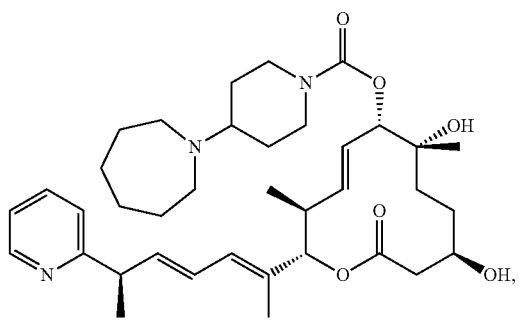

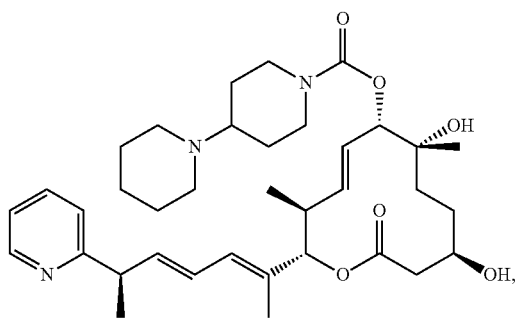

and pharmaceutically acceptable salts thereof.

A further purpose of the present invention is to provide pharmaceutical compositions comprising Compound 1, Compound 2, Compound 3, Compound 4, or a pharmaceutically acceptable salt thereof. Such pharmaceutical compositions may be formulated with one or more pharmaceutically acceptable carriers. Such compositions are formulated for use through various conventional routes of administration, including intravenous, oral, subcutaneous, or intramuscular administration.

The present invention may also relate to a method of treating a subject with cancer comprising administering to the subject an amount of Compound 1, Compound 2, Compound 3, Compound 4, or a pharmaceutically acceptable salt thereof, effective to produce a therapeutically beneficial response. The cancer may be myelodysplastic syndrome, leukemia such as chronic lymphocytic leukemia, acute lymphoblastic leukemia, chronic myelomonocytic leukemia, or acute myeloid leukemia, or a solid tumor such as colon cancer, pancreatic cancer, endometrial cancer, ovarian cancer, breast cancer, uveal melanoma, gastric cancer, cholangiocarcinoma, lung cancer, or any subset thereof. The cancer may test positive for one or more mutations in a spliceosome gene or protein, such as those listed in Table 1.

The present invention may also relate to the use of Compound 1, Compound 2, Compound 3, Compound 4, or a pharmaceutically acceptable salt thereof, in a method of therapeutic treatment, e.g., treatment for a cancer. The cancer may be myelodysplastic syndrome, leukemia such as chronic lymphocytic leukemia, acute lymphoblastic leukemia, chronic myelomonocytic leukemia, or acute myeloid leukemia, or a solid tumor such as colon cancer, pancreatic cancer, endometrial cancer, ovarian cancer, breast cancer, uveal melanoma, gastric cancer, cholangiocarcinoma, lung cancer, or any subset thereof. The cancer may test positive for one or more mutations in a spliceosome gene or protein, such as those listed in Table 1.

The present invention may also relate to the use of Compound 1, Compound 2, Compound 3, Compound 4, or a pharmaceutically acceptable salt thereof, in the preparation of a medicament. In particular, the medicament may be for the treatment of cancer. The cancer may be myelodysplastic syndrome, leukemia such as chronic lymphocytic leukemia, acute lymphoblastic leukemia, chronic myelomonocytic leukemia, or acute myeloid leukemia, or a solid tumor such as colon cancer, pancreatic cancer, endometrial cancer, ovarian cancer, breast cancer, uveal melanoma, gastric cancer, cholangiocarcinoma, lung cancer, or any subset thereof. The cancer may test positive for one or more mutations in a spliceosome gene or protein, such as those listed in Table 1.

The present invention further may relate to the use of Compound 1, Compound 2, Compound 3, Compound 4, or a pharmaceutically acceptable salt thereof, to target the spliceosome, e.g., subunit 1 of the SF3B spliceosome.

DETAILED DESCRIPTION OF CERTAIN EMBODIMENTS

A. Definitions

Figure 1:
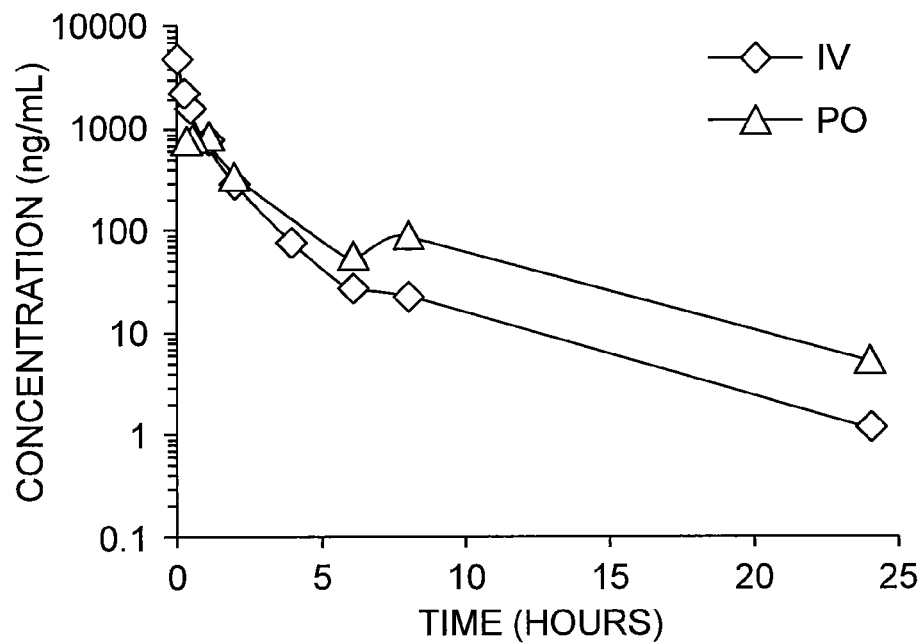
FIG. 1 shows the results of a pharmacokinetic (PK) study in CD-1 mice administered Compound 2 at doses of 5 mg/kg intravenous (IV) or 10 mg/kg oral administration (PO).

As used herein, the following definitions shall apply unless otherwise indicated.

"Isomers" refers to compounds having the same number and kind of atoms, and hence the same molecular weight, but differing with respect to the arrangement or configuration of the atoms. "Stereoisomers" refers to compounds that have the same atomic connectivity but different arrangements of their atoms in space. "Diastereoisomers" or "diastereomers" refers to stereoisomers that are not enantiomers. "Enantiomers" refers to stereoisomers that are non-superimposable mirror images of one another. "Geometric isomers" refers to cis-trans isomers having different positions of groups with respect to a double bond or ring or central atom.

Enantiomers taught herein may include "enantiomerically pure" isomers that comprise substantially a single enantiomer, for example, greater than or equal to 90%, 92%, 95%, 98%, or 99%, or equal to 100% of a single enantiomer, at a particular asymmetric center or centers. An "asymmetric center" or "chiral center" refers to a tetrahedral carbon atom that comprises four different substituents.

"Stereomerically pure" as used herein means a compound or composition thereof that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of diastereomers, and substantially free of the opposite enantiomer, of the compound. A typical stereomerically pure compound comprises greater than about 80% by weight of one stereoisomer of the compound and less than about 20% by weight of the other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. See, e.g., U.S. Pat. No. 7,189,715.

"R" and "S" as terms describing isomers are descriptors of the stereochemical configuration at an asymmetrically substituted carbon atom. The designation of an asymmetrically substituted carbon atom as "R" or "S" is done by application of the Cahn-Ingold-Prelog priority rules, as are well known to those skilled in the art, and described in the International Union of Pure and Applied Chemistry (IUPAC) Rules for the Nomenclature of Organic Chemistry. Section E, Stereochemistry.

"Treatment," "treat," or "treating" cancer refers to reversing (e.g., overcoming a differentiation blockage of the cells), alleviating (e.g., alleviating one or more symptoms, such as fatigue from anemia, low blood counts, etc.), and/or delaying the progression of (e.g., delaying the progression of the condition such as transformation to AML) a cancer as described herein.

"Subject", as used herein, means an animal subject, preferably a mammalian subject, and particularly human beings.

"Pharmaceutically acceptable carrier" as used herein refers to a nontoxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, cyclodextrins, sodium carboxymethylcellulose, polyacrylates, waxes, polyethylene-polyoxypropylene-block polymers, polyethylene glycol and wool fat.

A "pharmaceutically acceptable salt" is a salt that retains the desired biological activity of the parent compound and does not impart undesired toxicological effects. Examples of such salts are: (a) acid addition salts formed with inorganic acids, for example, hydrochloric acid, hydrobromic acid, sulfuric acid, phosphoric acid, nitric acid and the like; and salts formed with organic acids, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine. See, e.g., Haynes et al., "Commentary: Occurrence of Pharmaceutically Acceptable Anions and Cations in the Cambridge Structural Database," J. Pharmaceutical Sciences, vol. 94, no. 10 (2005), and Berge et al., "Pharmaceutical Salts", J. Pharmaceutical Sciences, vol. 66, no. 1 (1977), which are incorporated by reference herein.

B. Compounds

Unless otherwise stated, compounds depicted herein may include mixtures of the compound depicted herein, and any of enantiomeric, diastereomeric, and geometric (or conformational) forms of the structure; for example, the R and S configurations for each asymmetric center, (Z) and (E) double bond isomers, and (Z) and (E) conformational isomers. Unless otherwise stated, compounds depicted herein coexisting with tautomeric forms are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds may be useful, for example, as analytical tools or probes in biological assays.

Provided herein according to some embodiments is a compound of formula 1 ("Compound 1"), a compound of formula 2 ("Compound 2"), a compound of formula 3 ("Compound 3"), and a compound of formula 4 ("Compound 4"):

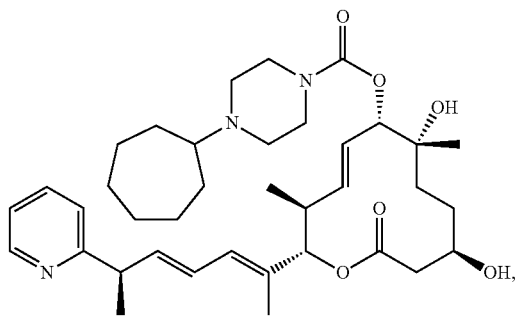

1

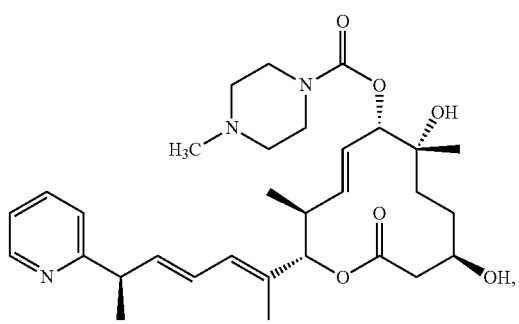

2

3

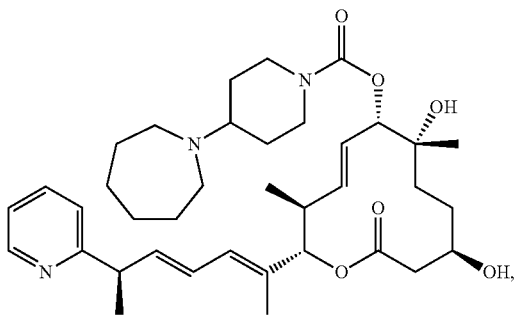

4

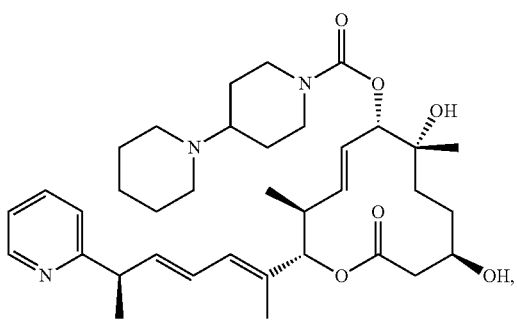

and pharmaceutically acceptable salts thereof.

C. Pharmaceutical Formulations

Compounds of the present invention can be combined with a pharmaceutically acceptable carrier to provide pharmaceutical formulations thereof. The particular choice of carrier and formulation will depend upon the particular route of administration for which the composition is intended.

The pharmaceutical compositions of the present invention may be suitably formulated for parenteral, oral, inhalation spray, topical, rectal, nasal, buccal, vaginal or implanted reservoir administration, etc. The term "parenteral" as used herein includes subcutaneous, intravenous, intramuscular, intra-articular, intra-synovial, intrasternal, intrathecal, intrahepatic, intralesional and intracranial injection or infusion techniques. In particular embodiments, the compounds are administered intravenously, orally, subcutaneously, or via intramuscular administration. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms, may also be used for the purposes of formulation.

For oral administration, a compound may be provided in an acceptable oral dosage form, including, but not limited to, capsules, tablets, aqueous suspensions or solutions. In the case of tablets for oral use, carriers commonly used include lactose and corn starch. Lubricating agents, such as magnesium stearate, may also be added. For oral administration in a capsule form, useful diluents include lactose and dried cornstarch. When aqueous suspensions are required for oral use, the active ingredient is combined with an emulsifying and/or suspending agent. If desired, certain sweetening, flavoring or coloring agents may also be added.

D. Subjects and Methods of Use

A compound of the present invention may be used to treat various types of cancers, including those responsive to agents that target SF3B1. As noted above, the anti-tumor activity of pladienolide B is reported as being connected to its targeting of the SF3b complex, inhibiting splicing and altering the pattern of gene expression (Kotake et al., "Splicing factor SF3b as a target of the antitumor natural product pladienolide," Nature Chemical Biology 2007, 3, 570-575). Mutations in spliceosome genes such as the Splicing factor 3B subunit 1 (SF3B1) protein are known to be implicated in a number of cancers, such as hematologic malignancies and solid tumors. Scott et al., "Acquired mutations that affect pre-mRNA splicing in hematologic malignancies and solid tumors," JNCI 105, 20, 1540-1549.

Hematological malignancies may include cancers of the blood (leukemia) or cancers of the lymph nodes (lymphomas). Leukemias may include acute lymphoblastic leukemia (ALL), acute myleogenous leukemia (AML), chronic lymphocytic leukemia (CLL), chronic myelogenous leukemia (CML), Chronic myelomonocytic leukemia (CMML), acute monocytic leukemia (AMoL), etc. Lymphomas may include Hodgkin's lymphoma and non-Hodgkin's lymphoma. Other hematologic malignancies may include myelodysplastic syndrome (MDS).

Solid tumors may include carcinomas such as adenocarcinoma, e.g., breast cancer, pancreatic cancer, prostate cancer, colon or colorectal cancer, lung cancer, gastric cancer, cervical cancer, endometrial cancer, ovarian cancer, cholangiocarcinoma, glioma, melanoma, etc.

A compound of the present invention may also be used to treat cancers that may be responsive to agents that target a spliceosome gene or protein other than SF3B1. The following examples are illustrative of some of the various cancers that may be responsive to agents that target the spliceosome, and are not meant to limit the scope of the invention in any way. Thus, compounds of the present invention may be administered to subjects to treat a variety of such cancers or conditions, such as patients or subjects afflicted with:

a) Myelodysplastic syndrome (MDS): See, e.g., "SF3B1 mutations in myelodysplastic syndromes: clinical associations and prognostic implications," Damm F. et al. Leukemia, 2011, 1-4; "Frequent pathway mutations in splicing machinery in myelodysplasia," Yoshida K. et al, Nature, 2011, 478, 64-69; "Clinical significance of SF3B1 mutations in myelodysplastic syndromes and myelodysplastic/myeloproliferative neoplasms," Malcovati L. et al., Blood, 2011, 118, 24, 6239-6246; "Mutations in the spliceosome machinery, a novel and ubiquitous pathway in leukemogenesis," Makishima et al, Blood, 2012, 119, 3203-3210; "Somatic SF3B1 mutation in myelodysplasia with ring sideroblasts," Pappaemannuil, E. et al, New England J. Med. 2011, DOI 10.1056/NEJMoa1103283.

b) Chronic lymphocytic leukemia (CLL): See, e.g., "Defects in the spliceosomal machinery: a new pathway of leukaemogenesis," Maciejewski, J. P., Padgett, R. A., Br. J. Haematology, 2012, 1-9; "Mutations in the SF3B1 splicing factor in chronic lymphocytic leukemia: associations with progression and fludarabine-refractoriness," Rossi et al, Blood, 2011, 118, 6904-6908; "Exome sequencing identifies recurrent mutations of the splicing factor SF3B1 gene in chronic lymphocytic leukemia," Quesada et al, Nature Genetics, 2011, 44, 47-52.

c) Chronic myelomonocytic leukemia (CMML): See, e.g., Yoshida et al, Nature 2011; "Spliceosomal gene mutations are frequent events in the diverse mutational spectrum of chronic myelomonocytic leukemia but largely absent in juvenile myelomonocytic leukemia," Kar S. A. et al, Haematologia, 2012, DOI: 10.3324/haematol.2012.064048; DeBoever et al., "Transcriptome sequencing reveals potential mechanism of cryptic 3' splice site selection in SF3B1-mutated cancers," PLOS Computational Biology, 2013, DOI: 10.1371/journal.pcbi.1004105.

d) Acute myeloid leukemia (AML): See, e.g., Malcovati et al., Blood 2011; Yoshida et al, Nature 2011.

e) Breast cancer: See, e.g., "Whole genome analysis informs breast cancer response to aromatase inhibition," Ellis et al., Nature, 2012, 486, 353-360; DeBoever et al., "Transcriptome sequencing reveals potential mechanism of cryptic 3' splice site selection in SF3B1-mutated cancers," PLOS Computational Biology, 2013, DOI: 10.1371/journal.pcbi.1004105; Maguire et al., "SF3B1 mutations constitute a novel therapeutic target in breast cancer," J Pathol 2015, 235, 571-580.

f) Uveal melanoma: See, e.g., "SF3B1 mutations are associated with alternative splicing in uveal melanoma," Furney et al., Cancer Disc. 2013, 10, 1122-1129; DeBoever et al., "Transcriptome sequencing reveals potential mechanism of cryptic 3' splice site selection in SF3B1-mutated cancers," PLOS Computational Biology, 2013, DOI: 10.1371/journal.pcbi.1004105.

g) Endometrial cancer: See, e.g., Tefferi et al., "Myelodysplastic syndromes." N Engl J Med. 2009; 361:1872-85.

h) Gastric cancer: See, e.g., Int J Cancer. 2013 July; 133(1):260-5, "Mutational analysis of splicing machinery genes SF3B1, U2AF1 and SRSF2 in myelodysplasia and other common tumors." Je et al.

i) Ovarian cancer: See, e.g., Int J Cancer. 2013 July; 133(1):260-5, "Mutational analysis of splicing machinery genes SF3B1, U2AF1 and SRSF2 in myelodysplasia and other common tumors." Je et al.

j) Biliary Tract cancers such as Cholangiocarcinoma and Pancreatic cancer: See, e.g., Biankin et al., "Pancreatic cancer genomes reveal aberrations in axon guidance pathway genes," Nature 2012, 491, 399-405.

k) Lung cancer: See, e.g., "Exome sequencing identifies recurrent mutations of the splicing factor SF3B1 gene in chronic lymphocytic leukemia," Quesada et al., Nature Genetics 44, 47-52 (2012); Scott et al., "Acquired mutations that affect pre-mRNA splicing in hematologic malignancies and solid tumors," JNCI 105, 20, 1540-1549.

In addition, the Catalogue of somatic mutations in cancer (COSMIC) (Wellcome Trust Sanger Institute, Genome Research Limited, England) reports SF3B1 mutations have been found in various types of cancer samples.

A compound of the present invention may be administered to a subject in a treatment effective or therapeutically effective amount. The amount of a compound of the present invention that may be combined with a carrier material to produce a composition in a single dosage form will vary depending upon the subject treated and the particular route of administration. Preferably, the compositions should be formulated so that a dosage of between 0.01-100 mg/kg body weight/day of the active agent can be administered to a subject receiving these compositions. In certain embodiments, the compositions of the present invention provide a dosage of from 0.01 mg to 50 mg. In other embodiments, a dosage of from 0.1 mg to 25 mg or from 5 mg to 40 mg is provided.

It should also be understood that a specific dosage and treatment regimen for any particular patient will depend upon a variety of factors, including the activity of the specific compound employed, the age, body weight, general health, sex, diet, time of administration, rate of excretion, drug combination, the judgment of the treating physician, and the severity of the particular disease being treated. The amount of active agent of the present invention in the composition will also depend upon the particular compound/salt in the composition.

In some embodiments, the cancer is tested for and/or is positive for one or more mutations in a spliceosome gene or protein, wherein the presence of the mutation(s) ("positive") may indicate the subject's cancer is responsive to a method of treatment comprising administration of a compound targeting this protein and/or the spliceosome. Examples of such spliceosome genes include, but are not limited to, those presented in Table 1.

TABLE 1

Spliceosome genes and potential diseases affected

| Spliceosome gene | Disease(s) |
| --- | --- |
| Splicing factor 3B subunit 1 (SF3B1) | see listings above |
| U2 small nuclear RNA auxiliary factor 1 (U2AF1) | MDS, AML, CMML, LUAD, UCEC |
| Serine/arginine-rich splicing factor 2 (SRSF2) | CMML, MDS, PMF, AML |
| | MDS |
| Zinc finger (CCCH type), RNA-binding motif and serine/arginine rich 2 (ZRSR2) | Retinitis Pigmentosa |
| Pre-mRNA-processing-splicing factor 8 (PRPF8) | Myeloid neoplasms |
| U2 Small Nuclear RNA Auxiliary Factor 2 (U2AF2) | MDS, PRAD, COAD |
| Splicing Factor 1 (SF1) | myeloid neoplasms, OV, COAD |
| Splicing factor 3a subunit 1 (SF3A1) | MDS |
| PRP40 pre-mRNA processing factor 40 homolog B (PRPF40B) | LUAD |
| RNA Binding Motif Protein 10 (RBM10) | COAD |
| Poly(rC) binding protein 1 (PCBP1) | SKCM |
| Crooked neck pre-mRNA splicing factor 1 (CRNKL1) | LUSC |
| DEAH (Asp-Glu-Ala-His) box helicase 9 (DHX9) | STAD |
| Peptidyl-prolyl cis-trans isomerase-like 2 (PPIL2) | SKCM |
| RNA binding motif protein 22 (RBM22) | LUAD |
| Small nuclear ribonucleoprotein Sm D3 (SNRPD3) | GBM, LGG |
| Probable ATP-dependent RNA helicase DDX5 (DDX5) | LUAD |

TABLE 1-continued

Spliceosome genes and potential diseases affected

| Spliceosome gene | Disease(s) |
|---|---|
| Pre-mRNA-splicing factor ATP-dependent RNA helicase DHX15 (DHX15) | DLBCL |
| Polyadenylate-binding protein 1 (PABPC1) | myeloid neoplasms |

Key:
MDS = Myelodysplastic syndrome
AML = Acute Myeloid Leukemia
CMML = chronic myelomonocytic leukemia
LUAD = Lung adenocarcinoma
UCEC = Uterine Corpus Endometrial Carcinoma
PMF = Progressive Massive Fibrosis
PRAD = Prostate adenocarcinoma
COAD = Colon adenocarcinoma
OV = Ovarian serous cystadenocarcinoma
SKCM = Skin Cutaneous Melanoma
LUSC = Lung squamous cell carcinoma
STAD = Stomach adenocarcinoma
GBM = Glioblastoma multiforme
LGG = Brain Lower Grade Glioma
DLBCL = Diffuse Large B-Cell Lymphoma In some embodiments, the subject's cancer may be responsive to a method of treatment comprising administration of a compound targeting this protein and/or the spliceosome even in the absence of such mutations in a spliceosome gene or protein.

Screening or testing for the mutations may be carried out by any known means, for example, genotyping, phenotyping, etc., by way of nucleic acid amplification, electrophoresis, microarrays, blot, functional assays, immunoassays, etc. Methods of screening may include, for example, collecting a biological sample from said subject containing the cancerous cells/tissue.

In order that the invention described herein may be more fully understood, the following examples are set forth. It should be understood that these examples are for illustrative purposes only and are not to be construed as limiting this invention in any manner.

EXAMPLES

Preparation of Compounds 1, 2, 3, and 4

General:

Microwave heating was done using a Biotage Emrys Liberator or Initiator microwave. Column chromatography was carried out using an Isco Rf200d. Solvent removal was carried out using either a Büchi rotary evaporator or a Genevac centrifugal evaporator. Preparative LC/MS was conducted using a Waters autopurifier and 19×100 mm XTerra 5 micron MS C18 column under acidic mobile phase condition. NMR spectra were recorded using a Varian 400 MHz spectrometer.

When the term "inerted" is used to describe a reactor (e.g., a reaction vessel, flask, glass reactor, and the like) it is meant that the air in the reactor has been replaced with an essentially moisture-free or dry, inert gas (such as nitrogen, argon, and the like).

General methods and experimentals for preparing compounds of the present invention are set forth below.

The following abbreviations are used herein:

MeOH: Methanol

DMF: Dimethylformamide

KHMDS: Potassium bis(trimethylsilyl)amide

LCMS: Liquid chromatography-mass spectrometry

TBSCl: tert-Butyldimethylsilyl chloride

THF: Tetrahydrofuran

TLC: Thin-layer chromatography

Materials: The following compounds are commercially available and/or can be prepared in a number of ways well known to one skilled in the art of organic synthesis. More specifically, disclosed compounds can be prepared using the reactions and techniques described herein. In the description of the synthetic methods described below, it is to be understood that all proposed reaction conditions, including choice of solvent, reaction atmosphere, reaction temperature, duration of the experiment, and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions are apparent to one skilled in the art, and alternate methods are therefore indicated. The starting materials for the examples are either commercially available or are readily prepared by standard methods from known materials.

LCMS information

Mobile phases: A (0.1% formic acid in $H_2O$) and B (0.1% formic acid in acetonitrile).

Gradient: B 5% →95% in 1.8 minutes.

Column: Acquity BEH C18 column (1.7 um, 2.1×50 mm).

U.S. Pat. Nos. 7,884,128 and 7,816,401, both entitled: Process for Total Synthesis of Pladienolide B and Pladienolide D, describe methods known in the art for synthesis of Pladienolide B and D. Synthesis of Pladienolide B and D may also be performed using methods known in the art and described in Kanada et al., "Total Synthesis of the Potent Antitumor Macrolides Pladienolide B and D," *Angew. Chem. Int. Ed.* 46:4350-4355 (2007). Kanada et al. and PCT application publication WO 2003/099813, entitled: Novel Physiologically Active Substances, describe methods known in the art for the synthesis of E7107 (Compound 45 of WO '813) from Pladienolide D (11107D of WO '813). A corresponding U.S. Pat. No. is 7,550,503 to Kotake et al.

Exemplary Synthesis of Compounds
Synthesis of Compound 1
Scheme I
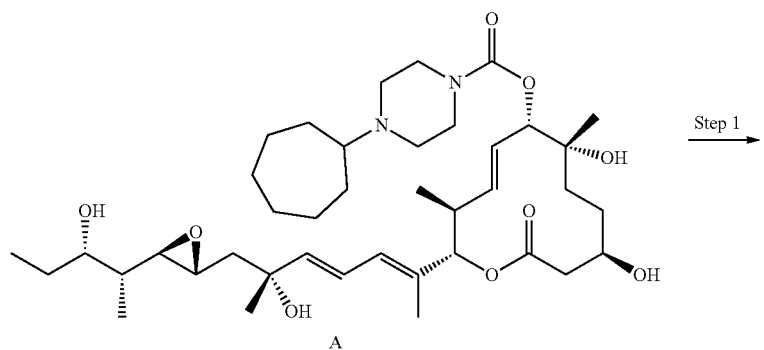
A
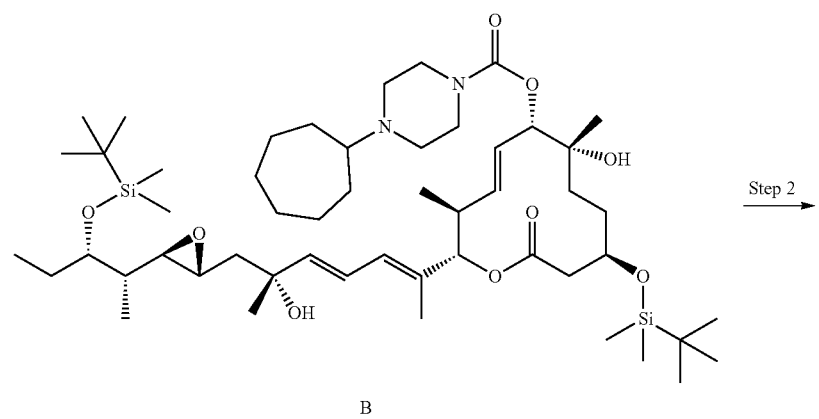
B
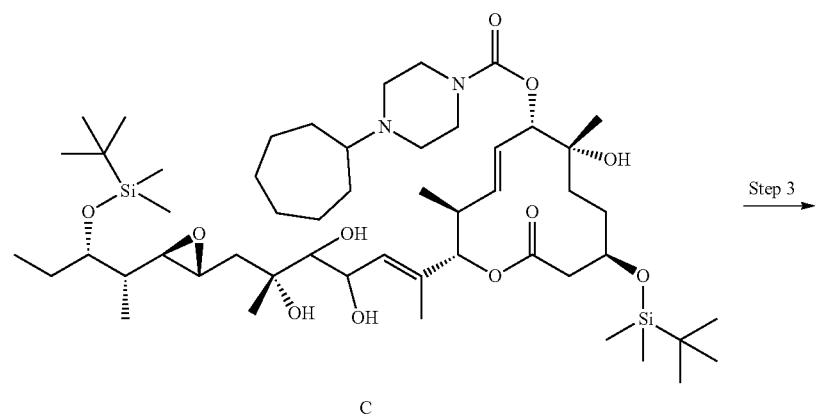
C

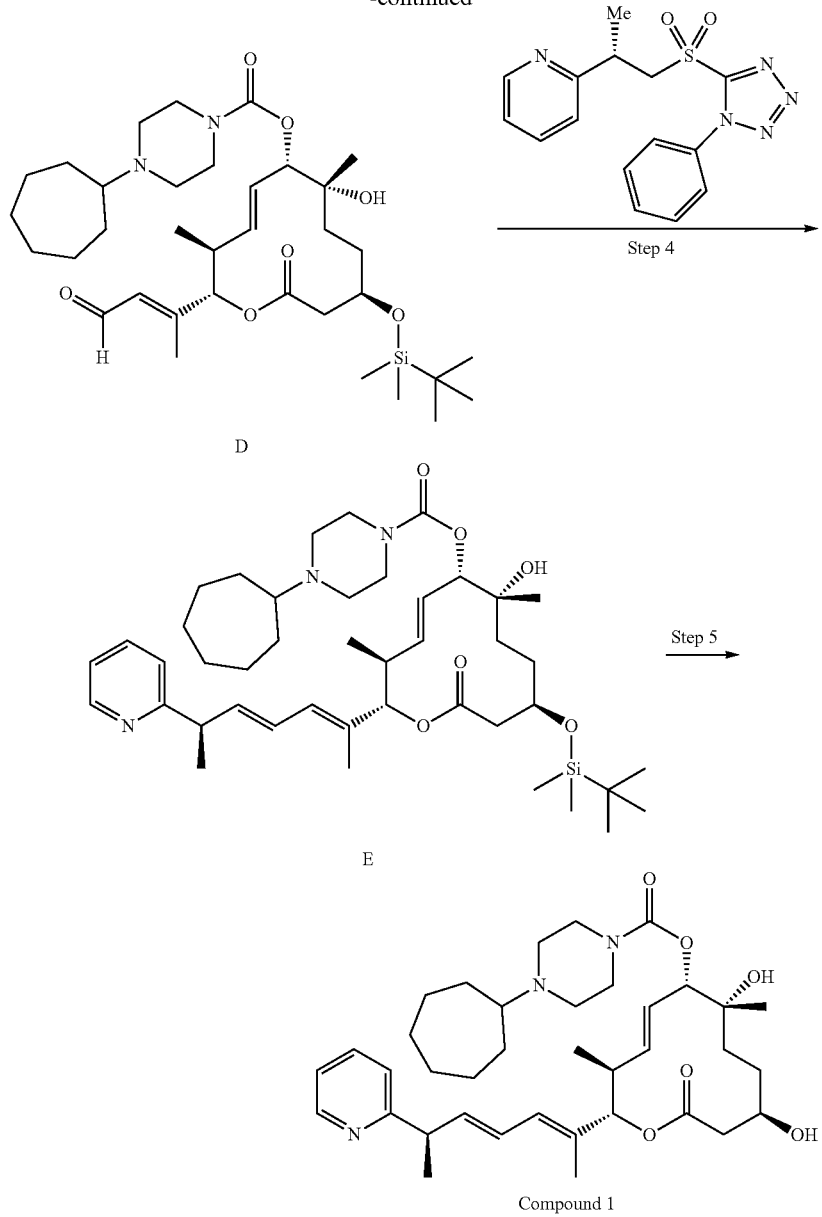

Step 1: Synthesis of (2S,3 S,6S,7R,10R,E)-10-((tert-butyldimethylsilyl)oxy)-((R,2E,4E)-7-((2R,3R)-3-((2S,3S)-3-((tert-butyldimethylsilyl)oxy)pentan-2-yl)-6-hydroxy-6-methylhepta-2,4-dien-2-yl)-7-hydroxy-3,7-dimethyl-12-oxooxacyclododec-4-en-6-yl 4-cycloheptylpiperazine-1-carboxylate. A solution of E7107 (A, 3.7 g, 5.1 mmol, 1.0 equiv.) under nitrogen in DMF (100 mL, 0.05M) at 0° C. was treated with imidazole (2.5 g, 36.1 mmol, 7.0 equiv.) and TBSCl (3.9 g, 25.7 mmol, 5.0 equiv.) was added. The reaction was allowed to warm to room temperature and stirred for 20 hours or until the reaction was determined to be complete by LCMS or TLC. The reaction was diluted with ethyl acetate and the organic layer was washed with brine, dried over sodium sulfate, filtered, and concentrated in vacuo. The resulting oil was purified by silica gel column chromatography (hexanes/ethyl acetate as eluent) to afford the desired product (B, 4.7 g, 5.0 mmol, 96%).

Step 2: Synthesis of (2S,3 S,6S,7R,10R,E)-10-((tert-butyldimethylsilyl)oxy)-2-((6R,E)-7-((2R,3R)-3-((2S,3S)-3-((tert-butyldimethylsilyl)oxy)pentan-2-yl)oxiran-2-yl)-4,5,6-trihydroxy-6-methylhept-2-en-2-yl)-7-hydroxy-3,7-dimethyl-12-oxooxacyclododec-4-en-6-yl 4-cycloheptylpiperazine-1-carboxylate. To a solution of olefin B (4.7 g, 5.0 mmol, 1.0 equiv.) in THF:H$_2$O (10:1, 133 mL:13 mL, 0.03M) under nitrogen at 0° C. was added osmium tetroxide (12.4 mL, 1.0 mmol, 0.2 equiv., 2.5% solution) followed by N-methylmorpholine N-oxide (1.16 g, 9.9 mmol, 2.0 equiv.). The reaction was allowed to warm to room temperature and stirred for 13 hours or until the reaction was determined to be complete by LCMS or TLC. The reaction was quenched with sodium sulfite, diluted with ethyl acetate, and the organic layer was washed with water, dried over magnesium sulfate, filtered, and concentrated in vacuo. The resulting oil was purified by silica gel column chromatography (dichloromethane/methanol as eluent) to afford the desired product (C, 4.8 g, 4.9 mmol, 99%).

Step 3: Synthesis of (2S,3S,6S,7R,10R,E)-10-((tert-butyldimethylsilyl)oxy-7-hydroxy-3,7-dimethyl-12-oxo-2-

((E)-4-oxobut-2-en-2-yl)oxacyclododec-4-en-6-yl 4-cycloheptylpiperazine-1-carboxylate. To a solution of diol C (4.4 g, 4.5 mmol, 1.0 equiv.) in benzene (100 mL, 0.05M) under nitrogen at room temperature was added lead tetraacetate (4.0 g, 9.0 mmol, 2.0 equiv.). The reaction was stirred for 30 minutes, or until the reaction was determined to be complete by LCMS or TLC. The reaction was quenched with sodium sulfite and diluted with dichloromethane. The organic layer was washed with water, dried over sodium sulfate, filtered, and concentrated in vacuo. The desired product (D, 1.5 g, 2.3 mmol, 52%) was advanced crude.

Step 4: Synthesis of (2S,3S,6S,7R,10R,E)-10-((tert-butyldimethylsilyl)oxy-7-hydroxy-3,7-dimethyl-12-oxo-2-4R, 2E,4E)-6-(pyridin-2-yl)hepta-2,4-dien-2-yl)oxacyclododec-4-en-6-yl 4-cycloheptylpiperazine-1-carboxylate.

Note: The synthesis of (S)-2-(1-((1-phenyl-1H-tetrazol-5-yl)sulfonyl)propan-2-yl)pyridine is described below and depicted in Scheme V.

To (S)-2-(1-((1-phenyl-1H-tetrazol-5-yl)sulfonyl)propan-2-yl)pyridine (1.67 g, 5.08 mmol, 2.5 equiv.) in dry THF (30.0 mL, 0.05M) under nitrogen at −78° C. was added KHMDS (8.53 ml, 4.265 mmol, 2.1 equiv.) dropwise and the reaction was stirred for 10 minutes. Then aldehyde D (2S,3S,6S,7R,10R,E)-10-((tert-butyldimethylsilyl)oxy)-7-hydroxy-3,7-dimethyl-12-oxo-2-((E)-4-oxobut-2-en-2-yl)oxacyclo-dodec-4-en-6-yl 4-cycloheptylpiperazine-1-carboxylate (1.318 g, 2.031 mmol, 1.0 equiv.) in THF (10 mL) was added dropwise. The reaction was stirred at −78° C. for one hour and then allowed to warm to room temperature overnight. The reaction was quenched with water and diluted with ethyl acetate. The organic layer was washed with water and brine, dried over magnesium sulfate, filtered, and concentrated in vacuo. The resulting oil was purified by silica gel column chromatography (hexane/ethyl acetate as eluent) to afford the desired product (E, 1.20 g, 2.03 mmol, 79%).

Step 5: Synthesis of (2S,3S,6S,7R,10R,E)-7,10-dihydroxy-3,7-dimethyl-12-oxo-2-((R,2E,4E)-6-(pyridin-2-yl)hepta-2,4-dien-2-yl)oxacyclododec-4-en-6-yl 4-cycloheptylpiperazine-1-carboxylate (compound 1). A solution of silyl ether E (1.80 g, 2.39 mmol, 1.0 equiv.) in MeOH (10.0 mL, 0.24M) under nitrogen at room temperature was treated with pTsOH (1.14 g, 5.98 mmol, 2.5 equiv.). The reaction was stirred for 2 hours, or until the reaction was determined to be complete by LCMS or TLC. The reaction was then diluted with ethyl acetate and washed with brine, dried over magnesium sulfate, filtered, and concentrated in vacuo. The resulting oil was purified by preparative TLC (dichloromethane/methanol as eluant) to afford the desired product (compound 1, 1.19 g, 1.83 mmol, 76%). $^1$H NMR (400 MHz, CHLOROFORM-d) δ: 0.88 (d, J=6.65 Hz, 6 H) 1.23 (s, 3 H) 1.34-1.78 (m, 12 H) 1.44 (d, J=7.03 Hz, 3 H) 1.73 (s, 3 H) 2.28-2.39 (m, 1 H) 2.45-2.66 (m, 8 H) 3.48 (br. s., 5 H) 3.72 (m, 2 H) 5.01 (d, J=9.54 Hz, 1 H) 5.14 (d, J=10.67 Hz, 1 H) 5.55-5.72 (m, 2 H) 6.00 (dd, J=15.00, 7.47 Hz, 1 H) 6.11 (d, J=11.29 Hz, 1 H) 6.28-6.35 (m, 1 H) 7.12 (ddd, J=7.47, 4.89, 1.07 Hz, 1H) 7.16 (d, J=7.78 Hz, 1 H) 7.61 (t, J=7.65 Hz, 1 H) 8.55 (d, J=4.91 Hz, 1 H). MS (ES+)=638.4 [M+H]$^+$.

Synthesis of Compound 2

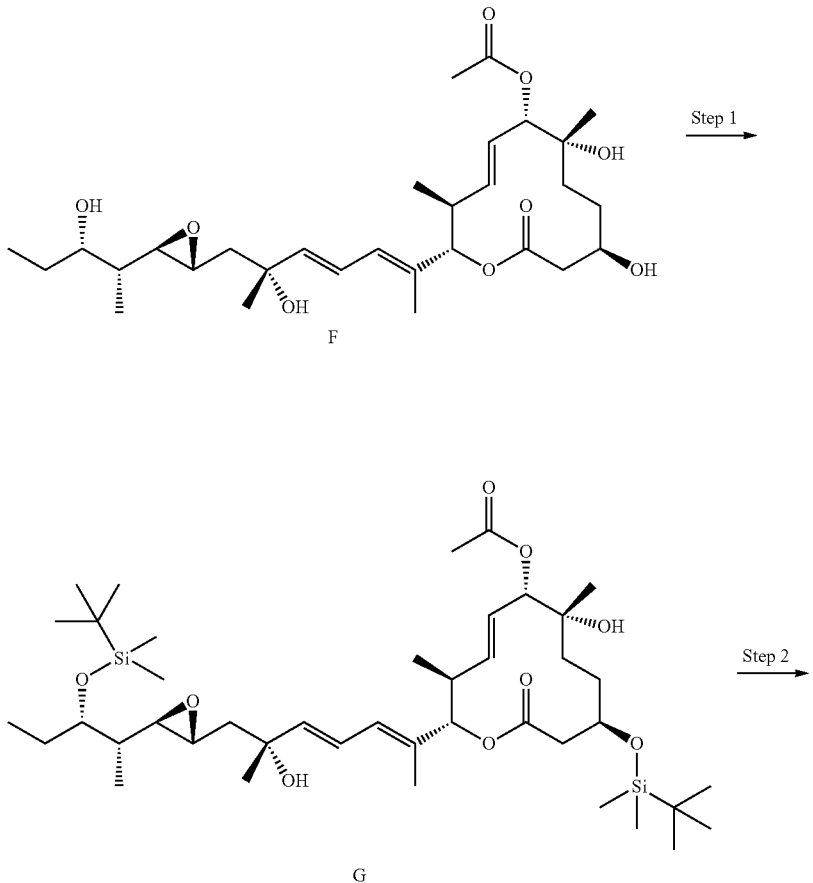

-continued
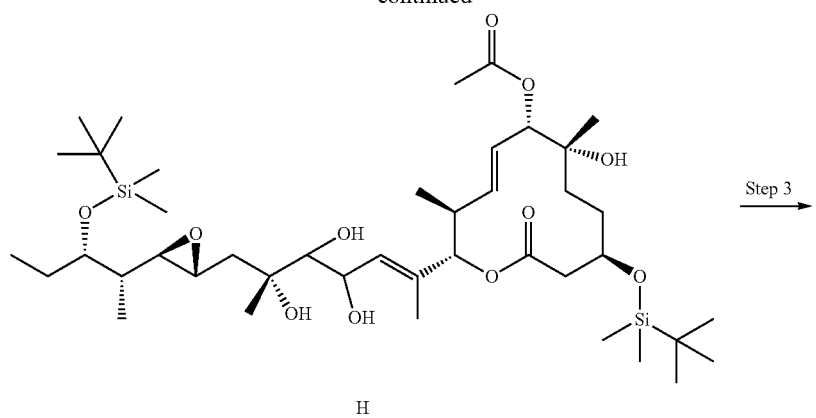
H
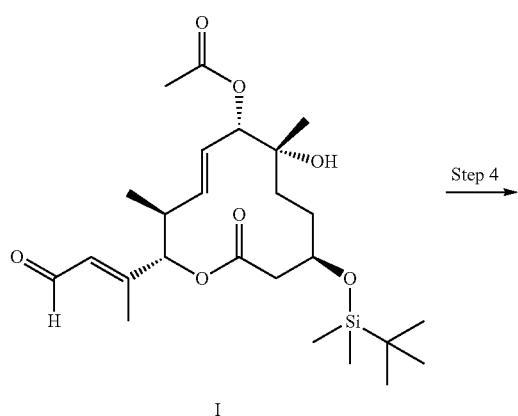
I
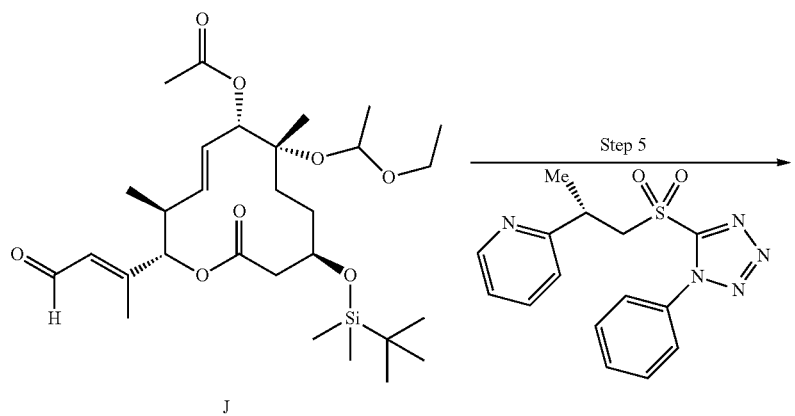
J
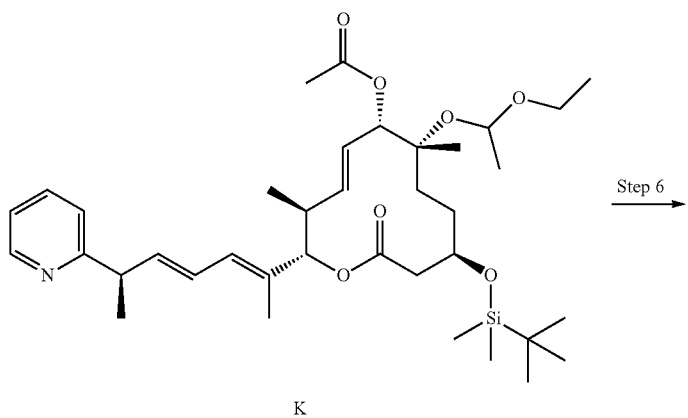
K

-continued

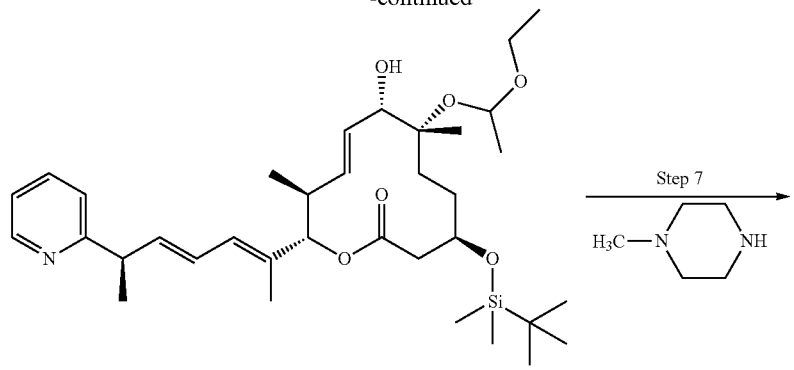

L

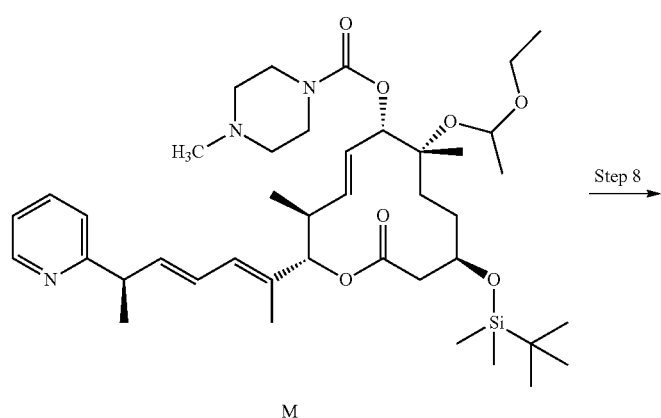

M

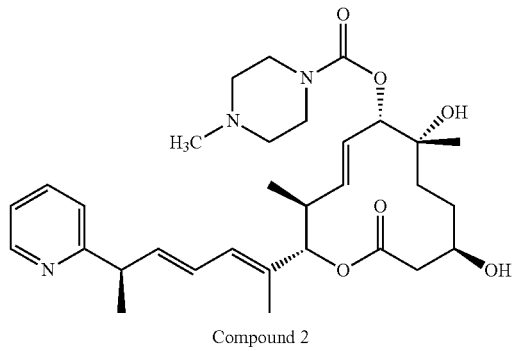

Compound 2

Step 1: Synthesis of (2S,3 S,6S,7R,10R,E)-10-((tert-butyldimethylsilyl)oxy)-2-((R,2E,4E)-7-((2R,3R)-3-((2S,3S)-3-((tert-butyldimethylsilyl)oxy)pentan-2-yl)oxiran-2-yl)-6-hydroxy-6-methylhepta-2,4-dien-2-yl)-7-hydroxy-3,7-dimethyl-12-oxooxacyclododec-4-en-6-yl acetate. A solution of pladienolide D (F, 5.3 g, 9.7 mmol, 1.0 equiv.) under nitrogen in DMF (80 mL, 0.1M) at 0° C. was treated with imidazole (4.6 g, 67.8 mmol, 7.0 equiv.) and TBSCl (7.3 g, 48.4 mmol, 5.0 equiv.). The reaction was allowed to warm to room temperature and stirred for 20 hours, or until the reaction was determined to be complete by LCMS or TLC. The reaction was extracted with ethyl acetate and the organic layer was washed with brine, dried over sodium sulfate, filtered, and concentrated in vacuo. The resulting oil was purified by silica gel column chromatography (hexanes/ethyl acetate as eluant) to afford the desired product (G, 7.5 g, 9.6 mmol, 99%).

Step 2: Synthesis of (2S,3 S,6S,7R,10R,E)-10-((tert-butyldimethylsilyl)oxy)-2-((6R,E)-7-((2R,3S)-3-((tert-butyldimethylsilyl)oxy)pentan-2-yl)oxiran-2-yl)-4,5,6-trihydrox-6-methylhept-2-en-2-yl)-7-hydroxy-3,7-dimethyl-12-oxooxacyclododec-4-en-6-yl acetate. To a solution of olefin G (7.6 g, 9.7 mmol, 1.0 equiv.) in degassed THF:H$_2$O (210 mL:21 mL, 0.01M) under nitrogen at 0° C. was added osmium tetroxide (24.4 mL, 1.9 mmol, 0.2 equiv., 2.5% solution in tert-butanol) followed by N-methylmorpholine N-oxide (2.3 g, 19.5 mmol, 2.0 equiv.). The reaction was allowed to warm to room temperature and stirred for 13 hours, or until the reaction was determined to be complete by LCMS or TLC. The reaction was quenched with sodium sulfite, diluted with ethyl acetate, and the organic layer was washed with water, dried over magnesium sulfate, filtered, and concentrated in vacuo. The resulting oil was purified by silica gel column chromatography (dichloromethane/methanol as eluent) to afford the desired product (H, 6.8 g, 8.3 mmol, 86%).

Step 3: Synthesis of (2S,3 S,6S,7R,10R,E)-10-((tert-butyldimethylsilyl)oxy)-7-hydroxy-3,7-dimethyl-12-oxo-2-((E)-4-oxobut-2-en-2-yl)oxacyclododec-4-en-6-yl acetate. To a solution of diol H (7.9 g, 9.7 mmol, 1.0 equiv.) in benzene (350 mL, 0.03M) under nitrogen at room temperature was added lead tetraacetate (8.6 g, 19.4 mmol, 2.0 equiv.). The reaction was stirred for 30 minutes, or until the reaction was determined to be complete by LCMS or TLC. The reaction was concentrated and purified by silica gel column chromatography (hexane/ethyl acetate as eluent) to afford the desired product (I, 2.5 g, 5.26 mmol, 54%).

Step 4: Synthesis of (2S,3S,6S,7R,10R,E)-10-((tert-butyldimethylsilyl)oxy)-7-(1-ethoxyethoxy)-3,7-dimethyl-12-oxo-2-((E)-4-oxobut-2-en-2-yl)oxacyclododec-4-en-6-yl acetate. To a solution of aldehyde I (1.4 g, 2.9 mmol, 1.0 equiv.) in THF (9.5 mL, 0.5M) was added ethoxyethene (11.1 mL, 40.0 equiv.) and pyridinium p-toluenesulfonate (0.07 g, 0.3 mmol, 0.1 equiv.) at room temperature. The reaction was stirred for 24 hours, or until the reaction was determined to be complete by LCMS or TLC. The reaction was quenched with sodium bicarbonate and diluted with ethyl acetate. The ethyl acetate was washed with water, brine, dried over magnesium sulfate, filtered, and concentrated in vacuo. The resulting oil was purified by silica gel column chromatography (hexane/ethyl acetate as eluent) to afford the desired product (J, 1.2 g, 2.2 mmol, 75%).

Step 5: Synthesis of (2S,3 S,6S,7R,10R,E)-10-((tert-butyldimethylsilyl)oxy)-7-(1-ethoxyethoxy)-3,7-dimethyl-12-oxo-2-((R,2E,4E)-6-(pyridin-2-yl)hepta-2,4-dien-2-yl)oxacyclododec-4-en-6-yl) acetate. To a solution of (S)-2-(1-((1-phenyl-1H-tetrazol-5-yl)sulfonyl)propan-2-yl)pyridine (695.0 mg, 2.1 mmol, 1.5 equiv.) in THF (20 mL, 0.06M) under nitrogen at −78° C. was added KHMDS (4.2 mL, 2.1 mmol, 1.5 equiv.) dropwise and the reaction was stirred for 20 minutes. Then aldehyde J (780.0 mg, 1.4 mmol, 1.0 equiv.) in THF (1.0 mL) was added dropwise. The reaction was stirred at −78° C. for 90 minutes and then allowed to warm to −20° C. for 1 hour. The reaction was quenched with ammonium chloride, diluted with ethyl acetate, and warmed to room temperature. The organic layer was washed with water, brine, dried over magnesium sulfate, filtered, and concentrated in vacuo. The resulting oil was purified by silica gel column chromatography (hexane/ethyl acetate as eluent) to afford the desired Julia product (K, 490 mg, 0.7 mmol, 53%).

Step 6: Synthesis of (4R,7R,8S,11S,E)-4-((tert-butyldimethylsilyl)oxy)-7-(1-ethoxyethoxy)-8-hydroxy-7,11-dimethyl-12-((R,2E,4E)-6-(pyridin-2-yl)hepta-2,4-dien-2-yl)oxacyclodec-9-en-2-one. To a solution of acetate K (490 mg, 0.7 mmol, 1.0 equiv.) in methanol (15 mL, 0.05M) at room temperature was added potassium carbonate (155 mg, 0.4 mmol, 1.5 equiv.). The reaction was run for 24 hours, or until the reaction was determined to be complete by LCMS or TLC. The reaction was quenched with water, diluted with ethyl acetate, washed with brine, dried over magnesium sulfate, filtered, and concentrated in vacuo. The resulting foamy solid (L, 459 mg, 0.7 mmol, 100%) was advanced into the next step without additional purification.

Step 7: Synthesis of (2S,3 S,6S,7R,10R,E)-10-((tert-butyldimethylsilyl)oxy)-7-(1-ethoxyethoxy)-3,7-dimethyl-12-oxo-2-((R,2E,4E)-6-(pyridin-2-yl)hepta-2,4-dien-2-yl)oxacyclododec-4-en-6-yl 4-methylpiperazine-1-carboxylate. To a solution of alcohol L (459 mg, 0.7 mmol, 1.0 equiv.) in dichloromethane (0.5 mL, 0.1M) at room temperature was added N,N-dimethylaminopyridine (27.3 mg, 0.2 mmol, 0.3 equiv.) and triethylamine (1.0 mL, 7.4 mmol, 10.0 equiv.) followed by 4-nitrophenyl chloroformate (451 mg, 02.2 mmol, 3.0 equiv.). The reaction was stirred at room temperature for three hours. Next, N-methyl-piperazine (299 mg, 2.98 mmol, 4.0 equiv.) was added at room temperature. After stirring for one hour, the reaction was quenched with water and diluted with dichloromethane. The organic layer was washed with 1N sodium hydroxide solution, and the organic layer was concentrated. The resulting oil was purified by silica gel column chromatography (hexanes/ethyl acetate as eluent) to afford the desired product (M, 553 mg, 0.75 mmol, 100%).

Step 8: Synthesis of (2S,3 S,6S,7R,10R,E)-7,10-dihydroxy-3,7-dimethyl-12-oxo-2-((R,2E,4E)-6-(pyridin-2-yl)hepta-2,4-dien-2-yl)oxacyclododec-4-en-6-yl 4-methylpiperazine-1-carboxylate (also named "(2S,3S,4E,6S,7R,10R)-7,10-dihydroxy-3,7-dimethyl-12-oxo-2-((2E,4E,6R)-6-(pyridin-2-yl)hepta-2,4- dien -2-yl)oxacyclododec-4-en-6-yl 4-methylpiperazine-1-carboxylate") (compound 2). To a solution of silyl ether (M, 553 mg, 0.74 mmol, 1.0 equiv.) in methanol (20 mL, 0.04M) at room temperature was added p-methoxytoluenesulfonic acid (425 mg, 2.2 mmol, 3.0 equiv.). The reaction was stirred for 3 hours, or until the reaction was determined to be complete by LCMS or TLC. The reaction was quenched with sodium bicarbonate and diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired product (compound 2, 184 mg, 0.33 mmol, 44%). $^1$H NMR (400 MHz, CHLOROFORM-d) δ: 0.82-1.00 (m, 3H) 1.22-1.48 (m, 8H) 1.50-1.63 (m, 1H) 1.66-1.83 (m, 4H) 1.97 (s, 1H) 2.07 (s, 1H) 2.33 (s, 3H) 2.40 (br. s., 311) 2.45-2.68 (m, 3H) 3.44-161 (m, 5H) 3.74 (dd, J=14.2, 7.2 Hz, 2H) 5.04 (d, J=9.3 Hz, 1H) 5.17 (d, J=10.5 Hz, 1H) 5.57-5.76 (m, 2H) 6.02 (dd, J=15.1, 7.5 Hz, 1H) 6.13 (d, J=10.8 Hz, 1H) 6.34 (ddd, J=15.1, 10.7, 1.0 Hz, 1H) 7.14 (t, J=6.2 Hz, 1H) 7.18 (d, J=7.4 Hz, 1H) 7.63 (t, J=7.3 Hz, 1H) 8.57 (d, J=5.1 Hz, 1H). MS (ES+)=556.4 [M+H].

Synthesis of Compound 3

Steps 1-6 are as provided above in the synthesis of Compound 2, to give alcohol L.

Scheme III

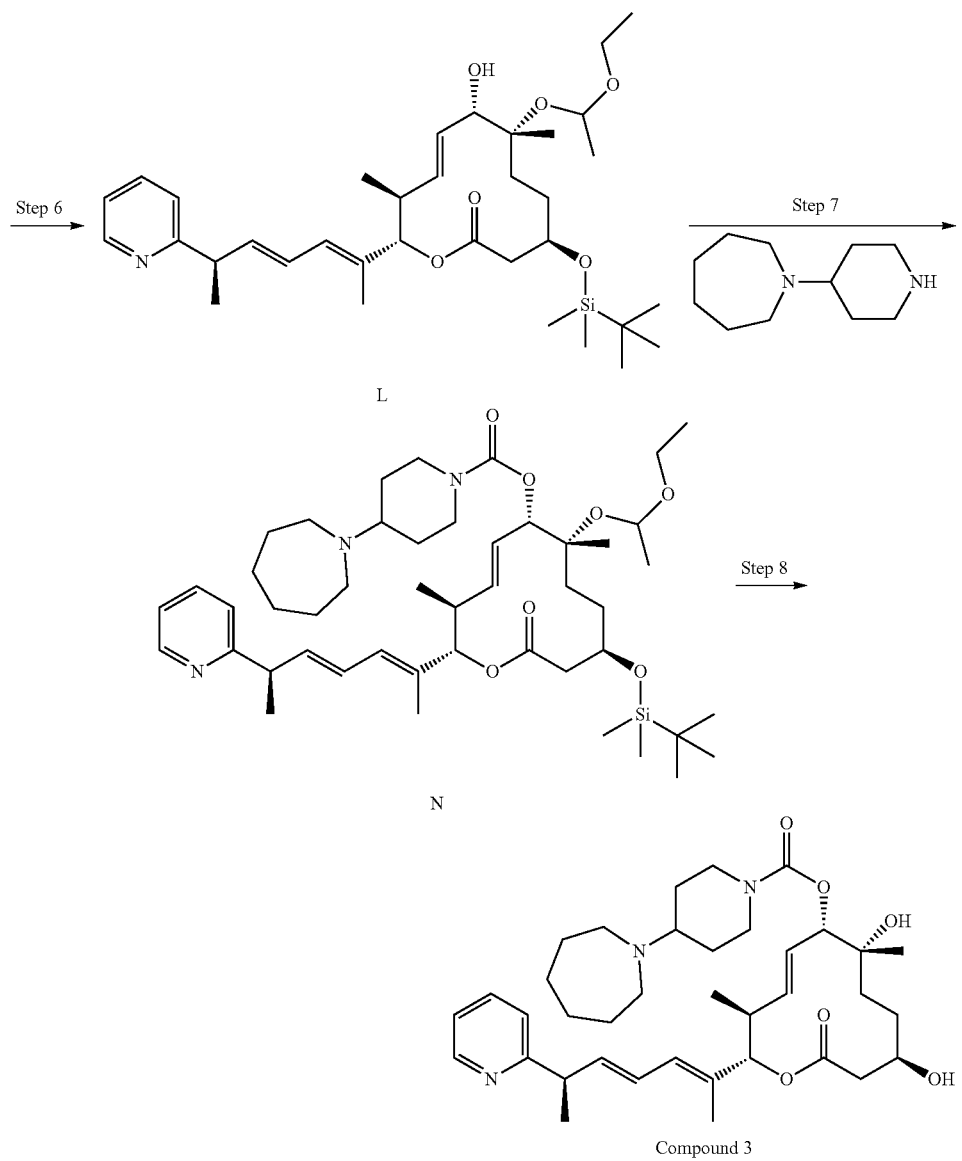

Step 7: Synthesis of (2S,3S,6S,7R,10R,E)-10-((tert-butyldimethylsilyl)oxy)-7-(1-ethoxyethoxy)-3,7-dimethyl-12-oxo-2-((R,2E,4E)-6-(pyridin-2-yl)hepta-2,4-dien-2-yl)oxacyclododec-4-en-6-yl 4-(azepan-1-yl)piperidine-1-carboxylate. To a solution of alcohol L (300 mg, 0.49 mmol, 1.0 equiv.) in dichloromethane (3.0 mL, 0.15M) at room temperature was added N,N-dimethylaminopyridine (71.4 mg, 0.58 mmol, 1.2 equiv.) and triethylamine (0.27 mL, 1.95 mmol, 4.0 equiv.) followed by 4-nitrophenyl chloroformate (196 mg, 0.97 mmol, 2.0 equiv.). The reaction was stirred at room temperature for three hours. Next, 1-(piperidin-4-yl)azepane (265 mg, 1.46 mmol, 3.0 equiv.) was added at room temperature. After stirring for one hour, the reaction was quenched with water and diluted with dichloromethane. The organic layer was washed with 1N sodium hydroxide solution, and the organic layer was concentrated. The resulting oil was purified by silica gel column chromatography (hexanes/ethyl acetate as eluent) to afford the desired product (N, 400 mg, 0.48 mmol, 100%).

Step 8: Synthesis of (2S,3S,6S,7R,10R,E)-7,10-dihydroxy-3,7-dimethyl-12-oxo-2-((R,2E,4E)-6-(pyridin-2-yl)hepta-2,4-dien-2-yl)oxacyclododec-4-en-6-yl 4-(azepan-1-yl)piperidine-1-carboxylate (compound 3). To a solution of silyl ether (N, 400 mg, 0.48 mmol, 1.0 equiv.) in methanol (4.0 mL, 0.1M) at room temperature was added p-methoxytoluenesulfonic acid (231 mg, 1.2 mmol, 2.5 equiv.). The reaction was stirred for 3 hours, or until the reaction was determined to be complete by LCMS or TLC. The reaction was quenched with sodium bicarbonate and diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired product (compound 3, 226 mg, 0.35 mmol, 73%). $^1$H NMR (400 MHz, CHLOROFORM-d) δ: 0.88 (d, J=6.53 Hz, 3 H) 1.20-1.28 (m, 4 H) 1.35 (s, 3 H) 1.45 (d, J=7.03 Hz, 4 H) 1.59 (br. s., 10 H) 1.74 (d, J=0.75

Hz, 3 H) 1.75-1.83 (m, 2 H) 1.99 (s, 1 H) 2.46-2.62 (m, 3 H) 2.62-2.71 (m, 4 H) 2.79 (br. s., 2 H) 3.51 (d, J=9.79 Hz, 1 H) 3.63-3.82 (m, 2 H) 4.03-4.26 (m, 2 H) 5.01 (d, J=9.54 Hz, 1 H) 5.16 (d, J=10.79 Hz, 1 H) 5.54-5.64 (m, 1 H) 5.65-5.75 (m, 1 H) 6.01 (dd, J=15.06, 7.53 Hz, 1 H) 6.12 (d, J=11.04 Hz, 1 H) 6.25-6.39 (m, 1 H) 7.12 (ddd, J=7.47, 4.83, 1.25 Hz, 1 H) 7.17 (dt, J=8.03, 1.00 Hz, 1 H) 7.62 (td, J=7.65, 1.76 Hz, 1 H) 8.56 (ddd, J=4.96, 1.82, 1.00 Hz, 1 H). MS (ES+)=638.6 [M+H].

Synthesis of Compound 4

Steps 1-6 are as provided above in the synthesis of Compound 2, to give alcohol L.

Step 7: Synthesis of (2S,3 S,6S,7R,10R,E)-10-((tert-butyldimethylsilyl)oxy)-7-(1-ethoxyethoxy)-3,7-dimethyl-12-oxo-2-4R,2E,4E)-6-(pyridin-2-yl)hepta-2,4-dien-2-yl)oxacyclododec-4-en-6-yl[1,4'-bipiperidine]-1'-carboxylate. To a solution of alcohol L (20 mg, 0.032 mmol, 1.0 equiv.) in dichloromethane (0.3 mL, 0.1M) at room temperature was added N,N-dimethylaminopyridine (4.8 mg, 0.04 mmol, 1.2 equiv.) and triethylamine (0.02 mL, 0.13 mmol, 4.0 equiv.) followed by 4-nitrophenyl chloroformate (13.1 mg, 0.065 mmol, 2.0 equiv.). The reaction was stirred at room temperature for three hours. Next, 1,4'-bipiperidine (16.4 mg, 0.97 mmol, 3.0 equiv.) was added at room temperature. After stirring for one hour, the reaction was quenched with water and diluted with dichloromethane. The organic layer was

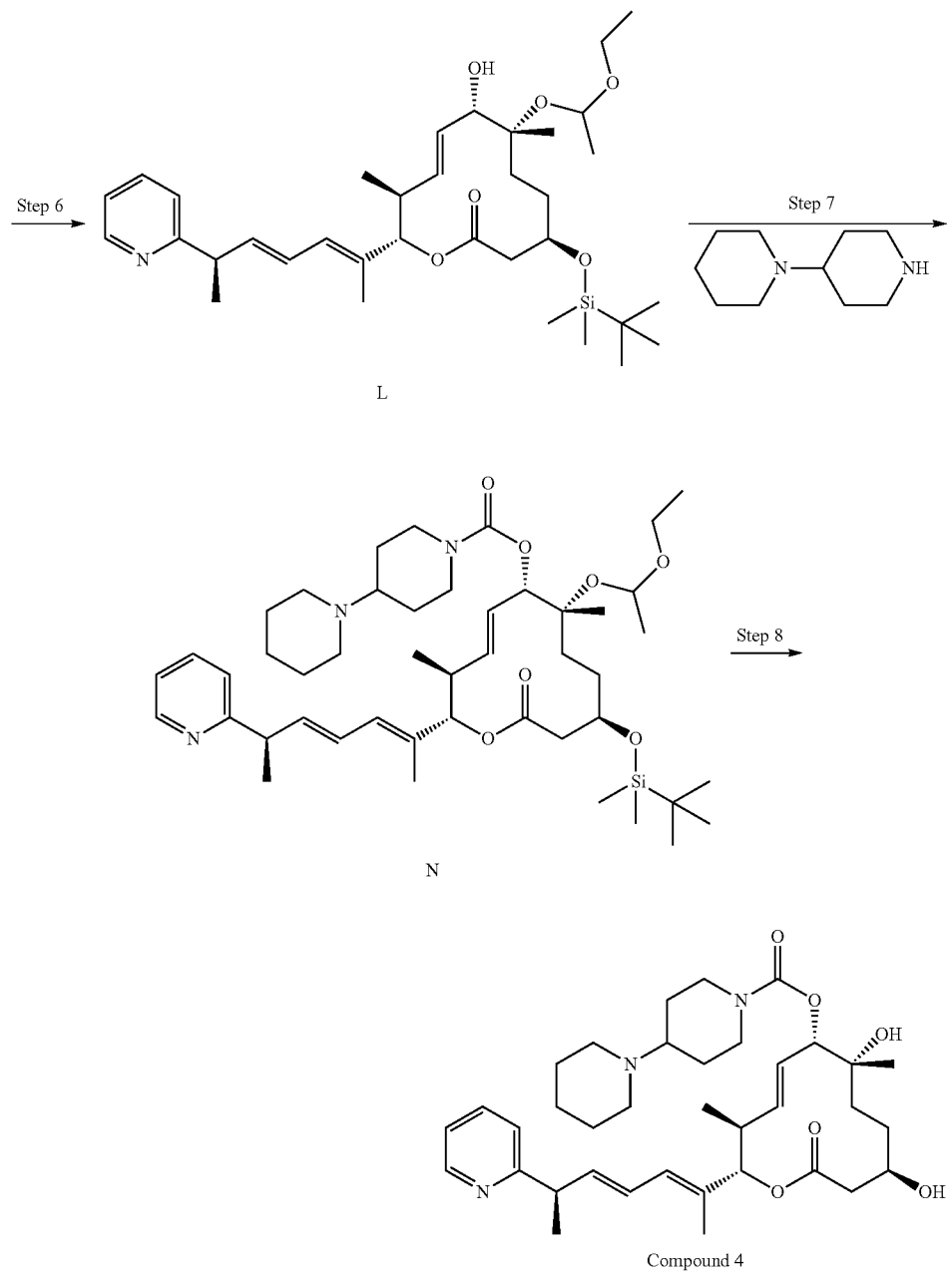

Scheme IV washed with 1N sodium hydroxide solution, and the organic layer was concentrated. The resulting oil was purified by silica gel column chromatography (hexanes/ethyl acetate as eluant) to afford the desired product (N, 18 mg, 0.22 mmol, 68.4%).

Step 8: Synthesis of (2S,3 S,6S,7R,10R,E)-7,10-dihydroxy-3,7-dimethyl-12-oxo-2-((R,2E,4E)-6-(pyridin-2-yl)hepta-2,4-dien-2-yl)oxacyclododec-4-en-6-yl[1,4'-bipiperidine]-1'-carboxylate (compound 4). To a solution of silyl ether (N, 18 mg, 0.022 mmol, 1.0 equiv.) in methanol (0.5 mL, 0.04M) at room temperature was added p-methoxytoluenesulfonic acid (10.6 mg, 0.56 mmol, 2.5 equiv.). The reaction was stirred for 3 hours, or until the reaction was determined to be complete by LCMS or TLC. The reaction was quenched with sodium bicarbonate and diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired product (compound 4, 4.0 mg, 0.006 mmol, 29%). $^1$H NMR (400 MHz, CHLOROFORM-d) δ: 0.90 (d, J=6.8 Hz, 3H) 1.17-1.42 (m, 5H) 1.46 (d, J=7.0 Hz, 6H) 1.51-1.65 (m, 6H) 1.65-1.78 (m, 5H) 1.85 (d, J=11.5 Hz, 2H) 2.44 (d, J=11.3 Hz, 2H) 2.49-2.66 (m, 6H) 2.80 (br. s., 2H) 3.42-3.62 (m, 1H) 3.63-3.82 (m, 2H) 4.18 (br. s., 2H) 5.02 (d, J=9.5 Hz, 1H) 5.17 (d, J=10.8 Hz, 1H) 5.57-5.75 (m, 2H) 6.02 (dd, J=15.2, 7.4 Hz, 1H) 6.14 (d, J=11.0 Hz, 1H) 6.34 (ddd, J=15.1, 10.8, 1.0 Hz, 1H) 7.14 (t, J=6.1 Hz, 1H) 7.18 (d, J=7.5 Hz, 1H) 7.29 (s, 2H) 7.63 (td, J=7.7, 1.9 Hz, 1H) 8.57 (d, J=5.1 Hz, 1H). MS (ES+)=624.6 [M+H].

Synthesis of (S)-2-(1-((1-phenyl-1H-tetrazol-5-yl)sulfonyl)propan-2-yl)pyridine

Scheme V

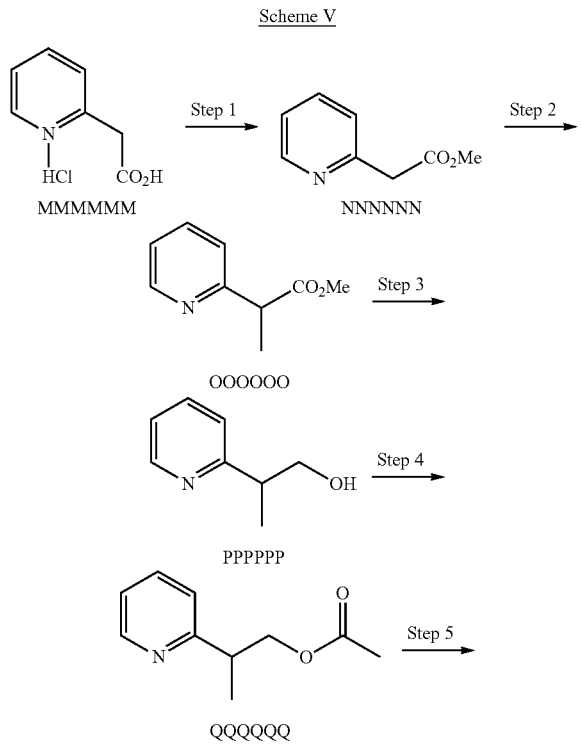

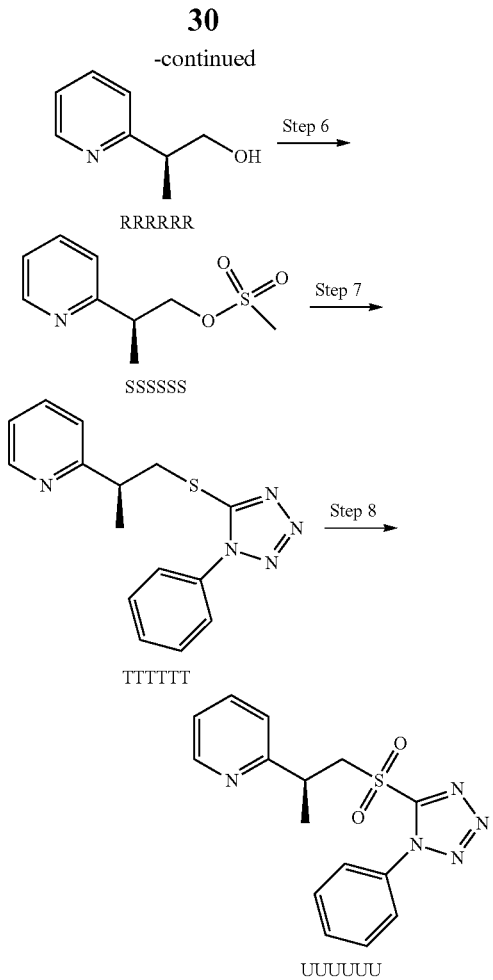

Step 1: To a solution of 2-(pyridin-2-yl)acetic acid hydrochloride salt MMMMMM (50.0 g, 288.0 mmol, 1.0 equiv.) in methanol (500 mL, 0.5M) at 0° C. was added thionyl chloride (31.5 mL, 432.0 mmol, 1.5 equiv.) dropwise. The reaction was stirred at 0° C. for 60 minutes or until the reaction was determined to be complete by LCMS or TLC. The reaction was carefully quenched with sodium carbonate and the aqueous layer extracted with ethyl acetate. The combined organic layers were washed with water, brine, dried over magnesium sulfate, filtered, and concentrated in vacuo. The resulting product (NNNNNN, 41.5 g, 275.0 mmol, 95%) was used in the next step without further purification.

Step 2: To a solution of ester NNNNNN (41.5 g, 275.0 mmol, 1.0 equiv.) in THF (1500 mL, 0.2M) at 0° C. was added sodium 2-methylpropan-2-olate (28.6 g, 288.3 mmol, 1.05 equiv.) and the reaction mixture was stirred for 30 minutes at 0° C. before addition of iodomethane (34.3 mL, 549.1 mmol, 2.0 equiv.). The reaction was stirred at room temperature for 1 hour or until the reaction was determined to be complete by LCMS or TLC. The reaction was quenched with ammonium chloride and the excess of solvent was removed in vacuo. The crude material was then extracted with ethyl acetate. The combined organic layers were washed with brine, and dried over magnesium sulfate. After filtration, the mixture was concentrated in vacuo. The resulting methyl ester (OOOOOO, 41.3 g, 250 mmol, 91%) was advanced without purification.

Step 3: To a solution of methyl ester OOOOOO (43.0 g, 260.3 mmol, 1.0 equiv.) in THF (1500 mL, 0.1M) at 0° C.

was added lithium aluminum hydride (312 mL, 312.4 mmol, 1.2 equiv., solution in THF) dropwise. The reaction was allowed to warm gradually to 0° C. for 30 minutes and then to room temperature for 1 hour or until the reaction was determined to be complete by LCMS or TLC. The reaction was carefully quenched with water, sodium hydroxide and water. After stirring the mixture for 30 minutes, the white precipitate was filtered off and the solvent was removed in vacuo. The reaction was then extracted with diethyl ether and the combined organic fractions were washed with water, brine, dried over magnesium sulfate, filtered, and concentrated in vacuo. The resulting alcohol (PPPPPP, 30.0 g, 219.0 mmol, 84%) was advanced without purification.

Step 4: To a solution of alcohol PPPPPP (30.0 g, 219.0 mmol, 1.0 equiv.) in dichloromethane (700 mL, 0.3M) at 0° C. was added triethylamine (61.5 mL, 437.4 mmol, 2.0 equiv), and DMAP (2.7 g, 21.9 mmol, 0.1 equiv.). Acetic anhydride (24.8 mL, 262.4 mmol, 1.2 equiv.) was added and the reaction mixture was stirred for 30 minutes or until the reaction was determined to be complete by LCMS or TLC. The reaction was quenched with ammonium chloride, the organic layer was washed with brine, dried over magnesium sulfate and filtered. The resulting solution was then evaporated and the crude acetate (QQQQQQ, 37.0 g, 206.0 mmol, 94%) was used in the following step without further purification.

Step 5: A solution of acetate QQQQQQ (39.4 g, 219.8 mmol, 1.0 equiv.) was dissolved in diethyl ether (100 mL) and then 118 g of silica gel was added. The excess of ether was removed in vacuo and the crude solid was then diluted in pH 7 aqueous buffer (1970 mL, 0.1M) (sodium hydroxyde/sodium phosphate monobasic/water). Porcine pancreatic lipase type II (3.3 g, (15 mg/mmol)) was added and the reaction was stirred at 37° C. for four hours or until determined to be complete by TLC or LCMS. (After four hours, conversion reached 40% according to ELSD and the enantiomeric excess was determined by chiral SFC, and showed an enantiomeric ratio of 13:1 S:R). (SFC condition: SFC Investigator (Waters/Thar), software: Chromscope v1.2, method: Isocratic 15% co-solvent 95:5 Heptane:IPA+ 0.1% DEA over 10 minutes, Column: Lux-Amylose-2, 4.6×250 mm, 5 µm, Total Flow: 4 ml/min (3.80 ml from CO$_2$ pump, 0.20 ml from modifier pump), Oven temp set to 35° C. and system pressure set to 100 bar, Retention Times: desired and major (S)-enantiomer 6.9 min, minor (R)-enantiomer 8.4 min) The silica gel was filtered off and the aqueous layer was extracted with ethyl acetate three times. The combined organic layers were washed with brine, dried over magnesium sulfate and concentrated. The product was purified by silica gel column chromatography (hexanes:ethyl acetate as eluant) to afford the desired alcohol (RRRRRR, 12.5 g, 91 mmol, 41%).

Step 6: To a solution of alcohol RRRRRR (12.5 g, 91.0 mmol, 1.00 equiv.) in dichloromethane (570 mL, 0.16M) at room temperature was added triethylamine (13.9 mL, 100.1 mmol, 1.1 equiv). The reaction was cooled down to 0° C. and then methanesulfonyl chloride (7.44 mL, 95.5 mmol, 1.05 equiv) was added. The reaction was stirred at 0° C. for 30 minutes or until determined to be complete by TLC or LCMS. The reaction was quenched with sodium bicarbonate and the layers were separated. The aqueous layer was then extracted with dichloromethane. The combined organic layers were washed with brine, dried over magnesium sulfate, and concentrated in vacuo. The resulting sulfonate SSSSSS (19.2 g, 89 mmol, 98%) was advanced without additional purification.

Step 7: To a solution of sulfonate SSSSSS (19.2 g, 89 mmol, 1.0 equiv.) in DMF (120 mL, 0.1M) at room temperature was added cesium carbonate (40.7 g, 125.0 mmol, 1.4 equiv.) and 1-phenyl-1H-tetrazole-5-thiol (19.1 g, 107.1 mmol, 1.2 equiv.). The resulting mixture was stirred at 50° C. for 48 hours, or until determined to be complete by TLC or LCMS. After cooling the mixture to room temperature, brine was added and the aqueous layer was extracted three times with diethyl ether. The combined organic layers were washed with water, brine, and dried over magnesium sulfate. After filtration, the solvent was removed in vacuo and the residue was purified using silica gel column chromatography (hexanes/ethyl acetate) to give the desired product (TTTTTT, 28.9 g, 88 mmol, 99%).

Step 8: To a solution of sulfide TTTTTT (31.5 g, 105.9 mmol, 1.0 equiv.) in EtOH (700 mL, 0.1M) at −10° C. was added ammonium molybdate tetrahydrate (6.5 g, 5.3 mmol, 0.05 equiv.) and hydrogen peroxide (108 mL, 1060 mmol, 5.0 equiv., 33% aqueous solution). The reaction was stirred at −10° C. for four hours or until determined to be complete by TLC or LCMS. The reaction was quenched with water and sodium metabisulfite solution. The crude product was collected by filtration and was purified by silica gel column chromatography (hexanes:ethyl acetate as eluant) to afford the desired product (UUUUUU, 23.2 g, 70.4 mmol, 66%). $^1$H NMR (400 MHz, CHLOROFORM-d) δ: 1.50 (d, J=7.03 Hz, 3 H) 1.66 (br. s., 1 H) 3.75 (m, 1 H) 3.94 (dd, J=14.81, 5.02 Hz, 1 H) 4.55 (dd, J=14.68, 7.91 Hz, 1 H) 7.14-7.22 (m, 2 H) 7.29 (s, 1 H) 7.57-7.70 (m, 6 H) 8.44-8.49 (m, 1 H).

The colorless oil was then recrystallized using toluene/heptane (1/1) (1 mL of toluene and 1 mL of heptane per 100 mg of compound. Heat gently the mixture to mix the two solvents. Let the mixture cool down to room temperature for 12 h. (If no recrystallization is observed, add one crystal to the solution. The crystal will help to get crystals via seeding process.) The crystals formed slowly over time. They could be isolated via filtration or removing liquid layer via pipette. The crystals were then washed with heptane and then quickly with toluene. The er of the sulfone was analized before and after recrystallization. (SFC conditions: SFC condition: SFC Investigator (Waters/Thar), software: Chromscope v1.2, method: Isocratic 10% co-solvent MeOH over 10 minutes, Column: ChiralPak IC, 4.6×250 mm, 5 um, Total Flow: 4 ml/min (3.80 ml from CO$_2$ pump, 0.20 ml from modifier pump), Oven temp set to 35° C. and system pressure set to 100 bar, Retention Times: desired and major (S)-enantiomer 3.5 min, minor (R)-enantiomer 3.8 min).

pH Stability Measurements

Compounds were provided in 96-well plates and tested in triplicate. Four microliters of a 10 mM stock solution of compound in DMSO were distributed into each of three wells. The plate was stored at or below −20° C. until the day of the analysis. Methanol (HPLC grade) and 0.1 N HCl (EMD catalog HX0603A-6) were used for dilutions. Acetonitrile (HPLC grade), water (Milli-Q filtered), trifluoroacetic acid (spectral grade) and 0.2M phosphate buffer (Wako, catalog no. 163-14471) were used to prepare the mobile phase for the two analyses.

Stability data was obtained using a Waters Acquity UPLC equipped with a UV detector (Waters TUV) and single quadrupole MS detector (Waters SQD). The 96-well plate containing the compound(s) of interest was(were) removed from the freezer and allowed to warm to room temperature for one hour. The UPLC was primed, equilibrated and the system performance was verified by injecting a standard.

After 1 hour, each of the three wells was diluted with 266 µL 0.1 N HCl to give pH=1. The plate was covered and placed on a shaker (Eppindorf Thermomixer R) for 45 minutes at 600 rpm. The plate was removed from the shaker, and the contents of each well were filtered through a filtration plate (Millipore catalog no. MSSLBPC50) by vacuum and injected into the UPLC. After approximately 24 hours, the contents of the wells were re-injected into the UPLC.

| UPLC Instrument Parameters (Solubility and Stability Measurement) | |
|---|---|
| Column | Acquity HSS T3 column, 2.1 × 100 mm, 1.8 µm |
| Mobile Phase | A = 0.05% TFA in Water B = 0.05% TFA in CH3CN |
| Elution Gradient | Time | Mobile Phase A:B |
| | 0.0 | 90/10 |
| | 0.75 | 3/97 |
| | 1.0 | 3/97 |
| | 1.01 | 90/10 |
| | 1.5 | 90/10 |
| Column temperature | 50° C. | |
| Detection | UV @ 220 nm | |
| Injection volume | 1 µL | |
| Flow rate | 0.9 mL/minute | |

Stability in the various buffers was measured by comparing the peak area- % of the analyte in methanol versus the peak area- % of the analyte at the same retention time in 0.1 N HCl buffer in the 24 hr time point injection. The stability assays reported in Table 2 show that compounds 1-4 have greater stability at pH 1 than compound E7107 over a 24-hour period.

TABLE 2

| Stability Assay Results | |
|---|---|
| Compound | % parent remaining (pH = 1, 24 hours) |
| E7107 | 44% |
| Compound 1 | 91% |
| Compound 2 | 96% |
| Compound 3 | 98% |
| Compound 4 | 99% |

Biological Assays

Cell Viability Assay Protocol

Cells (WiDr and Panc05.04 obtained from ATCC) were seeded in 96-well plates, with 2000 cells/100 µL/well, and incubated overnight. Spent media was removed, and fresh media containing 9 different concentrations of compound (100 µL/well) were added, with DMSO concentration from compound stock solution adjusted to be 0.1%. Each compound treatment was done in duplicate or triplicate at each concentration.

Another plate with cells seeded was dedicated as a time zero (Tz) plate, to which was added 0.1% DMSO in media (100 µL/well) followed by CellTiter-Glo® reagent (Promega Corporation, Madison, Wis.) (50 µL/well) for ATP measurement as a surrogate of cell viability. Average value from measurement of multiple wells of this plate is used as Tz.

Compound-treated plates were incubated for 72 hr at 37° C. Then, CellTiter-Glo® reagent (50 µL/well) was added and ATP was measured. Average value from measurement of the duplicate or triplicate compound-treated wells is used as Ti, and seeded plates with medium having 0.1% DMSO without compound is used as control growth (C).

Percentage growth inhibition/Percentage viability was calculated as:

$[(Ti-Tz)/(C-Tz)] \times 100$ for concentrations for which $Ti >/= Tz$ $[(Ti-Tz)/Tz] \times 100$ for concentrations for which $Ti < Tz$.

*time zero (Tz), control growth (C), and test growth in the presence of compound (Ti) Percentage growth inhibition/Percentage viability are plotted versus compound concentration to determine $E_{max}$.

Growth inhibition of 50% ($GI_{50}$) was calculated from $[(Ti-Tz)/(C-Tz)] \times 100=50$, which is the drug concentration resulting in a 50% reduction in the net increase of ATP in control growth (C) during the compound treatment.

In Vitro Splicing (Biochemical) Assay Protocol

Biotin-labeled pre-mRNA of an adenovirus type 2 construct with a deletion of intervening sequence (Ad2) (Berg, M. G., et al. 2012 Mol. Cell Bio., 32(7):1271-83) was prepared by in vitro transcription. The Ad2 construct containing Exon 1 (41 nucleotides), Intron (231 nucleotides), and Exon 2 (72 nucleotides) was generated by gene synthesis and cloned into the EcoRI and XbaI sites of pGEM®-3Z vector (Promega) by Genewiz® (South Plainfield, N.J.). The plasmid was then linearized by XbaI digestion and purified. In vitro transcription and purification of transcribed pre-mRNA were performed using the MEGAscript® T7 transcription kit (Invitrogen™, Life Technologies™, Grand Island, N.Y.) and MEGAclear™ transcription clean-up kit (Invitrogen™, Life Technologies™, Grand Island, N.Y.), respectively, following the manufacturer's instructions. The ratio of biotin-16-UTP (Roche Diagnostics Corporation, Indianapolis, Ind.) to cold UTP was 1:13 to incorporate approximately two biotin molecules per spliced Ad2 mRNA.

In vitro splicing assay was performed at 30° C. in 25 µL reaction mixtures containing 95 µg HeLa nuclear extract (Promega Corporation, Madison, Wis.), 47 nM Ad2 pre-mRNA, 25 U RNasin RNase inhibitor (Promega Corporation, Madison, Wis.), 1×SP buffer (0.5 mM ATP, 20 mM creatine phosphate, 1.6 mM $MgCl_2$), and compounds in DMSO (with 1% final concentration of DMSO). After 90 min of incubation, the reaction was stopped by addition of 18 µL of 5M NaCl, and the mixtures were incubated with 10 µL of M-280 streptavidin-coated magnetic beads (Invitrogen™, Life Technologies™, Grand Island, N.Y.) for 30 min at room temperature to capture Ad2 pre- and spliced mRNA. The beads were washed twice with 100 uL buffer containing 10 mM Tris pH=7.5, 1 mM EDTA and 2M NaCl, and then incubated in RNA gel loading buffer containing 95% formamide at 70° C. for 10 min to elute the RNAs. Ad2 RNAs were resolved by 6% TBE-UREA gel, transferred to a nylon membrane, UV cross-linked, and probed with an IRDye® labeled streptavidin (LI-COR, Lincoln, Nebr.). The amount of spliced RNA was quantified by measuring the band fluorescent intensity using LI-COR Image Studio software.

Results

Data are reported in Table 3 below. $E_{max}$ refers to the maximum achievable response to a compound in a tested dose range, with a negative value indicating cellular lethality. A larger negative $E_{max}$ value indicates greater cellular lethality for a particular compound. For example, in Panc 05.04 cells, a mutant SF3B1 cell line, the larger negative $E_{max}$ value indicates that Compound 1 had greater cellular lethality than Compound 2.

WiDr-R cells are colon cancer cells which have a chemically-induced R1074H mutation and have been shown to be resistant to pladienolide B in terms of growth inhibition (Yokoi, A., et al., 2011 FEBS Journal, 278:4870-4880). The counter-screening of compounds in this viability assay with a "resistant" WiDr-R cell line may indicate whether these compounds have off-target effect(s). Compounds that lack growth inhibitory ($GI_{50}$) activity in the resistant WiDr-R cell line but maintain activity in the parental WiDr cell line suggests that on-mechanism splicing modulation is responsible for the growth inhibition which is observed in the parental WiDr cell line.

The in vitro splicing (IVS) assay described above is a biochemical assay that monitors inhibition of the splicing of an exemplary pre-mRNA into an mRNA. This biochemical assay enables researchers to assess at what compound concentration splicing of this particular transcript is inhibited in a non-cellular context and is used to demonstrate mechanistic splicing inhibitory activity.

TABLE 3

Biological Activity of Compounds 1, 2, 3 and 4

| Compound number | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | In vitro splicing (IVS) assay (nM) |
|---|---|---|---|---|---|
| 1 | −86.85 | 19.48 | 15.85 | >1000 | 188.00 |
| 2 | −66.09 | 32.72 | 31.78 | >1000 | 1330.00 |
| 3 | −90.81 | 20.75 | 26.29 | >1000 | 770.00 |
| 4 | −86.16 | 11.81 | 12.98 | >1000 | 89.00 |

Key
Panc 05.04 cells: Pancreatic cancer cells, mutant SF3B1 cell line (Q699H and K700E mutations in SF3B1)
WiDr cells: Colon cancer cells (wildtype SF3B1)
WiDr-R cells: Colon cancer cells (chemically-induced SF3B1 mutant which is resistant to E7107 (R1074H mutation))

Additional Testing of Compounds

Mouse Pharmacokinetic (PK) Study

Compound 2 was dosed at 5 mg/kg IV (intravenous) or 10 mg/kg PO (oral administration) to CD-1 mice. Following administration, blood samples were collected at pre-determined time points from five mice via serial bleeding of the tail vein. Blood was collected at 0.083 (0.167 PO only), 0.5, 1, 2, 4, 6, 8, and 24 hours post administration. The blood samples were centrifuged at 5000 RPM for 5 minutes to collect plasma within 30 minutes of blood collection. After extraction, samples were assayed using LCMS. PK parameters were calculated using non-compartmental analysis in WinNonlin v6.3.

The data indicated that Compound 2 shows oral bioavailability and favorable pharmacokinetic properties in the mouse model (FIG. 1, Table 4).

TABLE 4

| Pharmacokinetic Property | Dose | |
|---|---|---|
| | 5 mg/kg IV | 10 mg/kg PO |
| $C_{max}$ (ng/mL) | NA | 840.73 |
| $C_{max}/D$ (ng/mL/D) | NA | 84.07 |
| $t_{max}$ (h) | NA | 1.00 |
| $t_{1/2}$ (h) | 3.88 | 4.04 |
| $AUC_{0-t}$ (ng · h/mL) | 3156.95 | 2513.35 |
| $AUC_{0-inf}$ (ng · h/mL) | 3163.56 | 2544.86 |
| $AUC_{0-inf}/D$ (ng · h/mL/D) | 632.71 | 254.49 |

TABLE 4-continued

| Pharmacokinetic Property | Dose | |
|---|---|---|
| | 5 mg/kg IV | 10 mg/kg PO |
| CL (L/kg/h) | 1.58 | NA |
| Vss (L/kg) | 2.37 | NA |
| % F | NA | 40.22 |

Mouse Xenograft Model

The efficacy of Compound 2 was tested in a mouse xenograft model. Nalm-6 SF3B1$^{K700E}$ isogenic cells (human pre B-cell line, 10×10$^6$ cells) were subcutaneously implanted into the flank of female CB17-SCID mice. Mice were treated with Compound 2 (10% ethanol, 5% TWEEN-80, 85% saline) or vehicle control. The animals were orally dosed daily for 14 days (QD×14 PO) at the amounts indicated in FIG. 2 and were monitored until they reached either of the following endpoints: 1) excessive tumor volume measured three times a week (tumor volume calculated by using the ellipsoid formula: (length×width$^2$)/2); or 2) development of any health problems such as paralysis or excessive body weight loss. All animal studies were carried out according to the H3 Biomedicine Guide for the Care and Use of Laboratory Animals.

Figure 2:
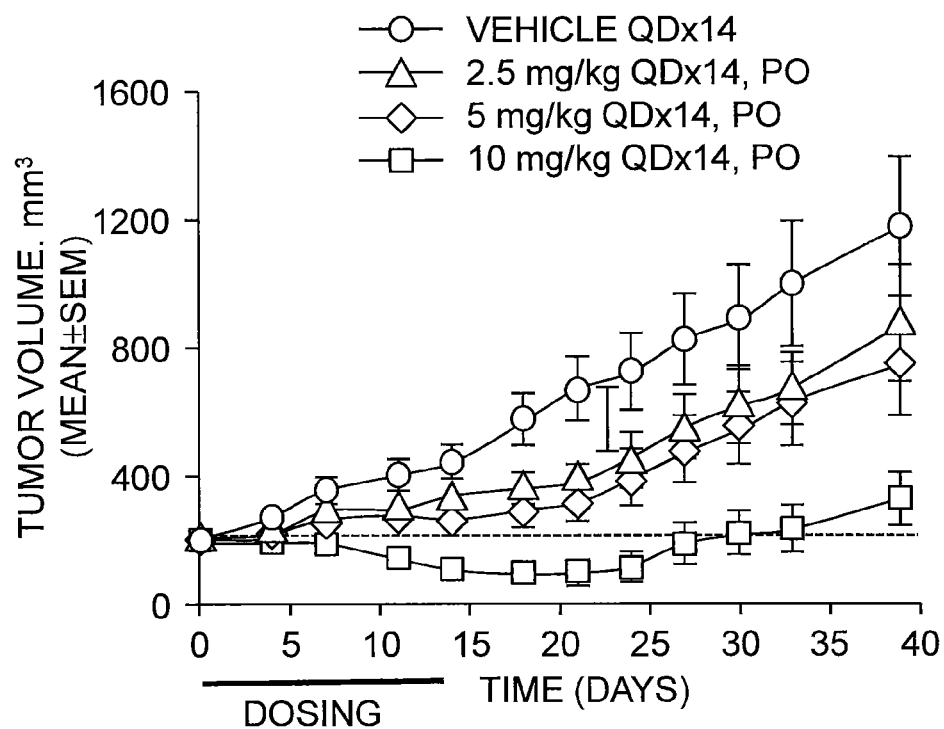
FIG. 2 shows the efficacy of Compound 2 in a Nalm-6 (human pre B-cell line) mouse xenograft model with an engineered SF3B1$^{K700E}$ mutation. Mice were administered 2.5, 5, or 10 mg/kg Compound 2 once daily (QD) for 14 days, and tumor volume was measured over a 40 day period.

The results indicated that Compound 2 was efficacious when administered via the oral route and reduced tumor growth in the xenograft mouse model (FIG. 2).

PK/PD Testing in Mouse Xenograft Model

Pharmacokinetics (PK)/pharmacodynamics (PD) of Compound 2 were also analyzed in the Nalm-6 mouse xenograft model. Nalm-6 SF3B1$^{K700E}$ isogenic cells (human pre B-cell line, 10×10$^6$ cells) were subcutaneously implanted into the flank of female CB17-SCID mice. Mice were administered a single oral dose of 10 mg/kg Compound 2 (10% ethanol, 5% TWEEN-80, 85% saline), and the tumors were collected at the indicated times post administration for analysis.

RNA was isolated using RiboPure™ RNA purification kit (Ambion®) and used for qPCR analysis. The RNA was retrotranscribed according to the instructions of the SuperScript® VILO™ cDNA synthesis kit (Invitrogen™), and 0.04 μl of cDNA was used for quantitative PCR (qPCR). qPCR for pre-mRNA EIF4A1 and mature mRNA SLC24A19 and PK evaluation were performed as reported previously (Eskens, F. A. et al. Phase I pharmacokinetic and pharmacodynamic study of the first-in-class spliceosome inhibitor E7107 in patients with advanced solid tumors. Clin Cancer Res. 19, 6296-6304, doi:10.1158/1078-0432.CCR-13-0485 (2013)). All animal studies were carried out according to the H3 Biomedicine Guide for the Care and Use of Laboratory Animals.

Figure 3:
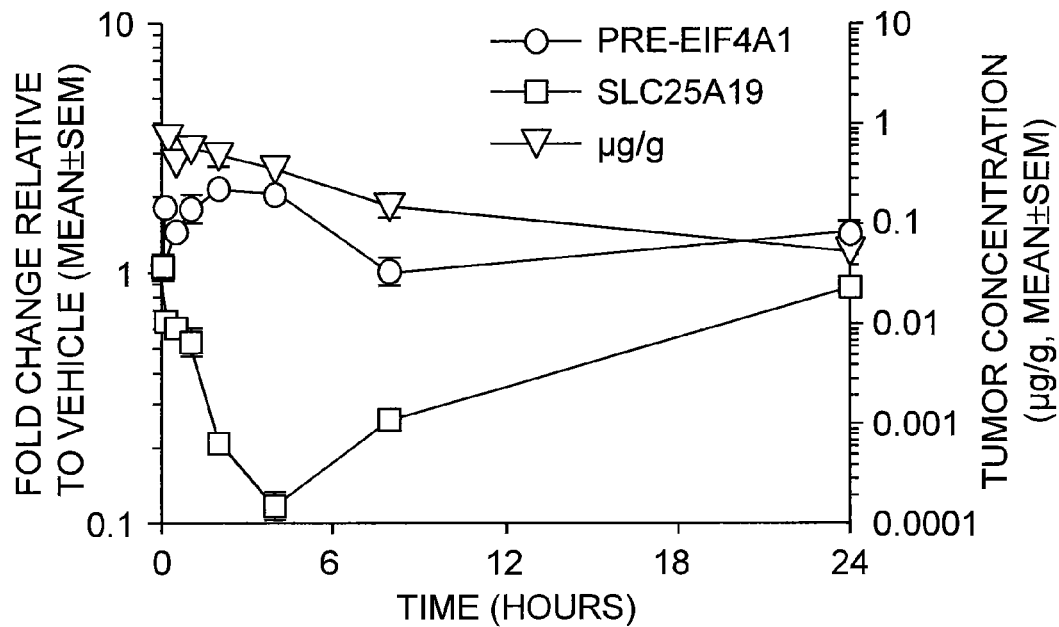
FIG. 3 shows pharmacokinetic and pharmacodynamic analysis of Compound 2 in a Nalm-6 (human pre B-cell line) xenograft model with an engineered SF3B1$^{K700E}$ mutation. Mice were administered a 10 mg/kg PO dose of Compound 2, and tumor concentration (µg/g) and fold change in expression of Pre-EIF4A1 (the pre-mRNA of the EIF4A1 transcript) and SLC25A19 (the mature mRNA of the SLC25A19 transcript) relative to vehicle were determined.

The results shown in FIG. 3 indicated that Compound 2 showed PD responses at a tolerated dose via the oral route of administration.

Cellular Viability Assay

Figure 4:
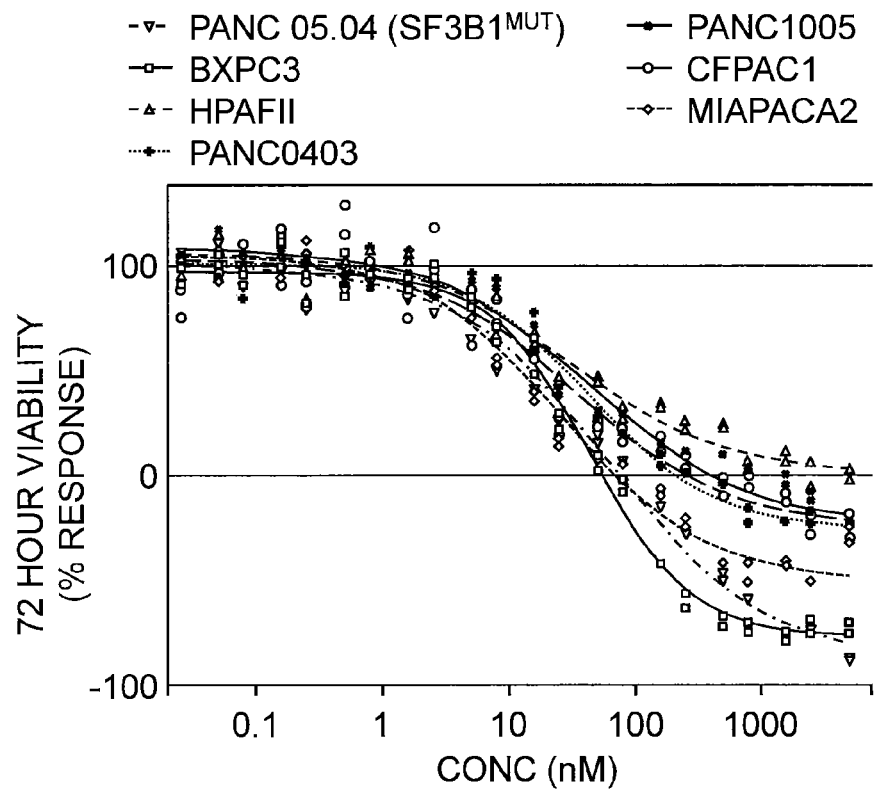
FIG. 4 shows the results of a cellular viability assay with Compound 2 in the PANCO504 cancer cell line (SF3B1$^{MUT}$) (mutant PANC 05.04) compared with wild-type SF3B1 pancreatic cancer cell lines BXPC3, HPAFII, PANC0403, PANC1005, CFPAC1 and MIAPACA2.

To assess the viability of Panc 05.04 cancer cells (SF3B1$^{MUT}$) (Q699H and K700E mutations in SF3B1) in the presence of Compound 2, cells were seeded at 750 cells per well in a 384-well plate and treated with Compound 2 at the concentrations indicated in FIG. 4 for 72 hours at 37° C. The relative number of viable or apoptotic cells were measured by luminescence using CELLTITER-GLO® luminescent Cell Viability Assay (Promega).

The results indicated differential cellular lethality in the mutant SF3B1 pancreatic cancer cell line over wild-type SF3B1 pancreatic cancer cell lines (FIG. 4).

Comparison of Alternative Splicing for E7107 and Compound 2

The modulation of alternative splicing for E7107 and Compound 2 was determined using the nCounter® analysis system (NanoString Techologies, Inc., Seattle, Wash.). Nalm-6 isogenic cells were treated with Compound 2 or E7107 (obtained from Eisai, Inc.) at 10×GI$_{50}$ for 6 hours. RNA was isolated using RiboPure™ RNA purification kit (Ambion®) and used for analysis. The RNA was retrotranscribed according to the instructions of the SuperScript® VILO™ cDNA synthesis kit (Invitrogen™) and 0.04 µl of cDNA was used for qPCR.

Figure 5:
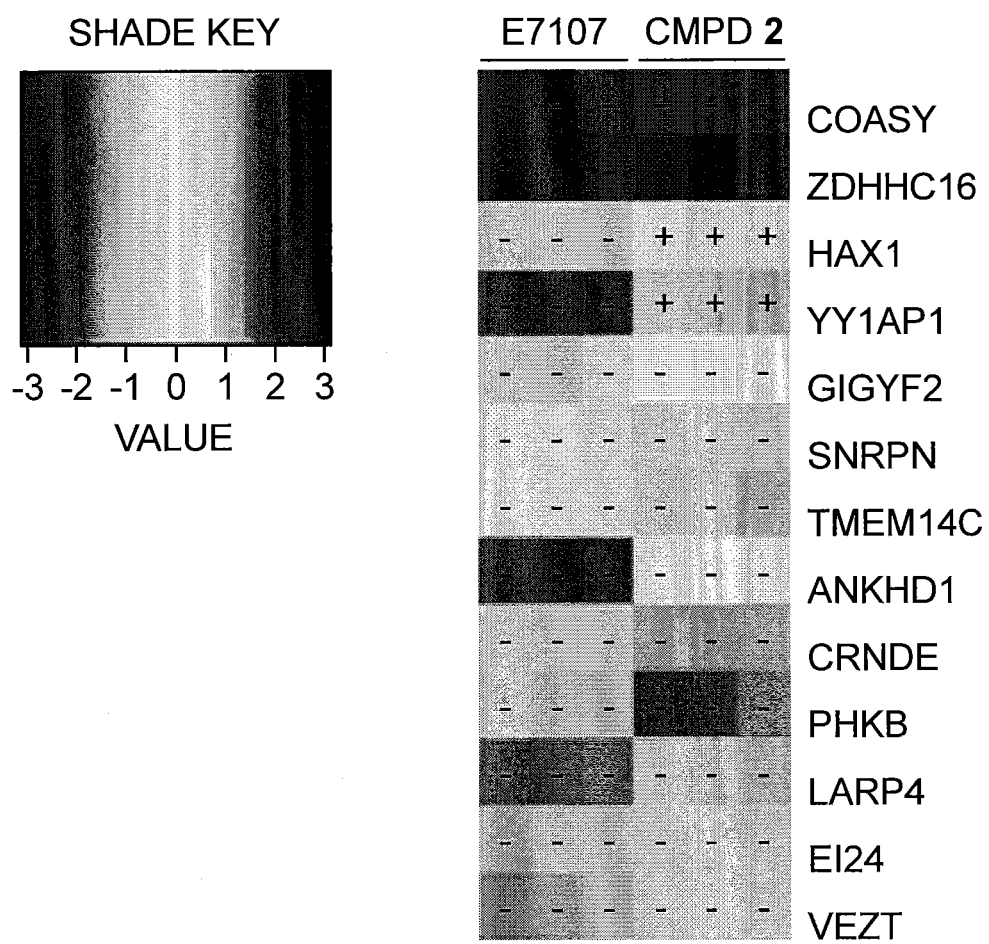
FIG. 5 shows the modulation of alternative splicing for E7107 and Compound 2 (cmpd 2) based on Nanostring analysis. The "+" and "−" indicate positive or negative values, respectively, in the shade key, which indicates the varying levels of expression of the different splice junctions.

Results shown in FIG. 5 indicated that the splicing modulation profile for Compound 2 is distinct from the profile of E7107.

Mouse Pharmacokinetic (PK) Study of Compound 1

Compound 1 was dosed at 5 mg/kg IV or 12 mg/kg PO to CD-1 mice. Following administration, blood samples were collected at pre-determined time points from five mice via serial bleeding from the tail vein. Blood was collected at 0.083 (0.167 PO only), 0.5, 1, 2, 4, 6, 8, and 24 hours post-dose. The blood samples were centrifuged at 5000 RPM for 5 minutes to collect plasma within 30 minutes of blood collection. After extraction, samples were assayed using LCMS. PK parameters were calculated using non-compartmental analysis in WinNonlin v6.3.

Figure 6:
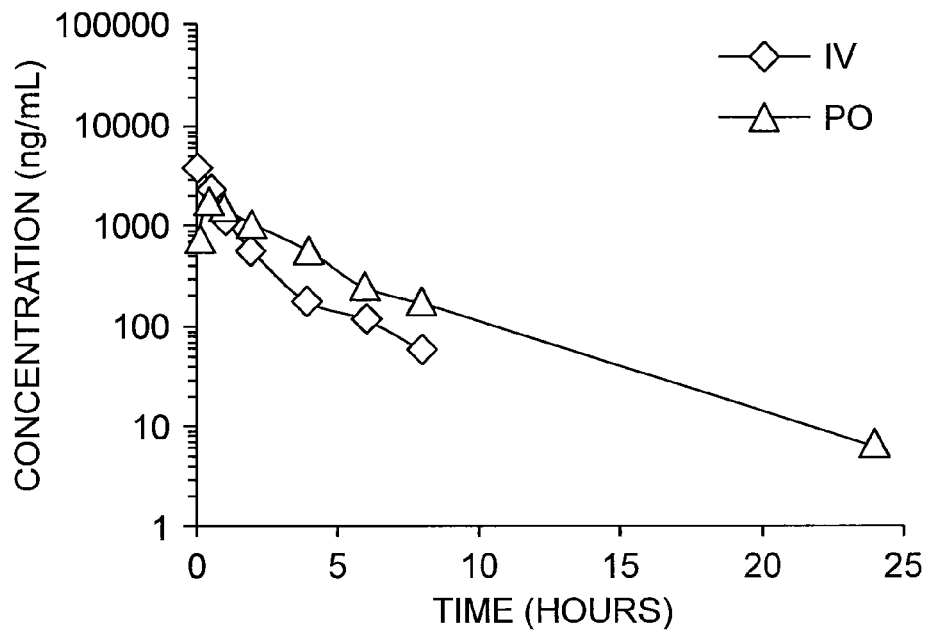
FIG. 6 shows the results of a PK study in CD-1 mice administered Compound 1 at doses of 5 mg/kg intravenous (IV) or 12 mg/kg oral administration (PO).

The data indicated that Compound 1 showed oral bioavailability and favorable pharmacokinetic properties in the mouse model (FIG. 6, Table 5).

TABLE 5

| Pharmacokinetic Property | Dose | |
|---|---|---|
| | 5 mg/kg IV | 12 mg/kg PO |
| $C_{max}$ (ng/mL) | NA | 1810.81 |
| $C_{max}/D$ (ng/mL/D) | NA | 141.47 |
| $t_{max}$ (h) | NA | 0.50 |
| $t_{1/2}$ (h) | 2.54 | 3.00 |
| $AUC_{0-t}$ (ng · h/mL) | 4453.75 | 6206.20 |
| $AUC_{0-inf}$ (ng · h/mL) | 4670.80 | 6234.38 |
| $AUC_{0-inf}/D$ (ng · h/mL/D) | 934.15 | 487.06 |
| CL (L/kg/h) | 1.07 | NA |
| Vss (L/kg) | 2.10 | NA |
| % F | NA | 52.14 |

Efficacy of Compound 1 in a Mouse Xenograft Model

The efficacy of Compound 1 was tested in a mouse xenograft model. Nalm-6 SF3B1$^{K700E}$ isogenic cells (human pre B-cell line, 10×10$^6$ cells) were subcutaneously implanted into the flank of female CB17-SCID mice. Mice were treated with Compound 1 (10% ethanol, 5% TWEEN-80, 85% saline) or vehicle control. The animals were orally dosed daily for 14 days (QD×14 PO) with 7.5 mg/kg or 10 mg/kg Compound 1 or vehicle and were monitored until they reached either of the following endpoints: 1) excessive tumor volume measured three times a week (tumor volume calculated by using the ellipsoid formula: (length×width$^2$)/2); or 2) development of any health problems such as paralysis or excessive body weight loss. All animal studies were carried out according to the H3 Biomedicine Guide for the Care and Use of Laboratory Animals.

Figure 7:
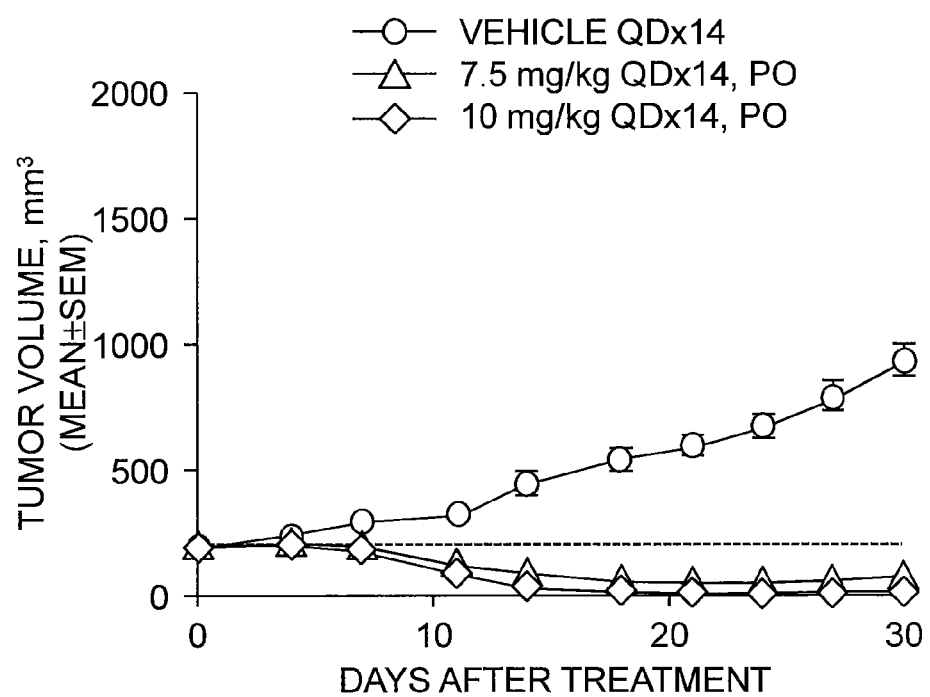
FIG. 7 shows the efficacy of Compound 1 in a Nalm-6 mouse xenograft model with an engineered SF3B1$^{K700E}$ mutation. Mice were administered 7.5 or 10 mg/kg Compound 1 once daily (QD) for 14 days, and tumor volume was measured over a 30 day period.

The results indicated that Compound 1 was efficacious when administered via the oral route and reduced tumor growth in the xenograft mouse model (FIG. 7).

PK/PD Testing of Compound 1 in Mouse Xenograft Model

Pharmacokinetics (PK)/pharmacodynamics (PD) of Compound 1 were also analyzed in the Nalm-6 mouse xenograft model. Nalm-6 SF3B1$^{K700E}$ isogenic cells (human pre B-cell line, 10×10$^6$ cells) were subcutaneously implanted into the flank of female CB17-SCID mice. Mice were administered a single oral dose of Compound 1 (10% ethanol, 5% TWEEN-80, 85% saline), and the tumors were collected at the indicated times post administration for analysis.

RNA was isolated using RiboPure™ RNA purification kit (Ambion®) and used for qPCR analysis. The RNA was retrotranscribed according to the instructions of the SuperScript® VILO™ cDNA synthesis kit (Invitrogen™), and 0.04 µl of cDNA was used for quantitative PCR (qPCR). qPCR for pre-mRNA EIF4A1 and mature mRNA SLC24A19 and PK evaluation were performed as reported previously (Eskens, F. A. et al. Phase I pharmacokinetic and pharmacodynamic study of the first-in-class spliceosome inhibitor E7107 in patients with advanced solid tumors. Clin Cancer Res. 19, 6296-6304, doi:10.1158/1078-0432.CCR-13-0485 (2013)). All animal studies were carried out according to the H3 Biomedicine Guide for the Care and Use of Laboratory Animals.

Figure 8:
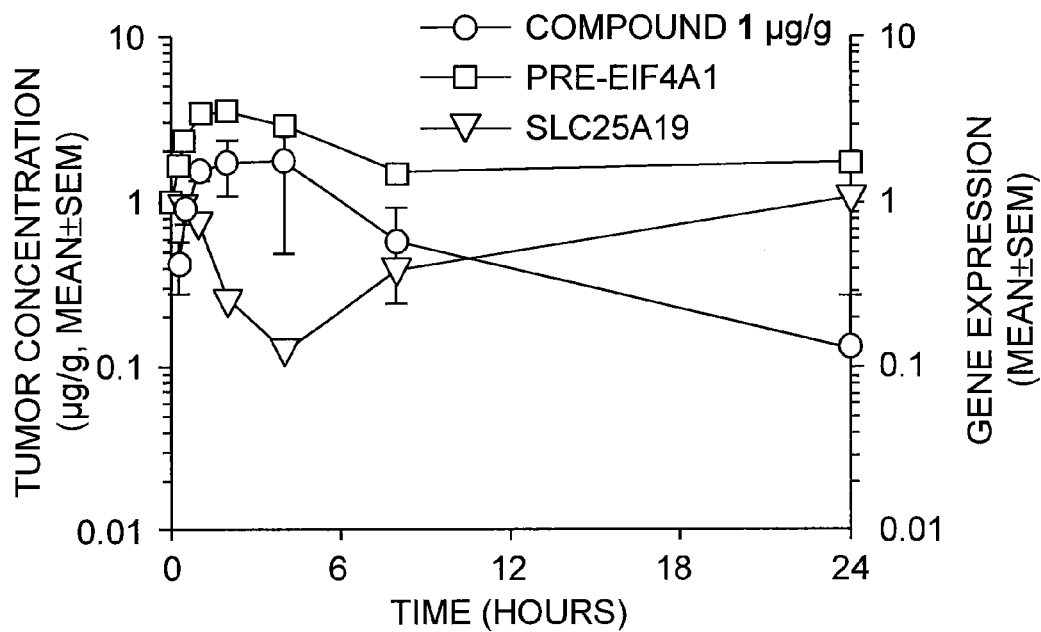
FIG. 8 shows pharmacokinetic and pharmacodynamic analysis of Compound 1 in a Nalm-6 xenograft model with an engineered SF3B1$^{K700E}$ mutation. Mice were administered a single PO dose of Compound 1, and tumor concentration (µg/g) and fold change in expression of Pre-EIF4A1 (the pre-mRNA of the EIF4A1 transcript) and SLC25A19 (the mature mRNA of the SLC25A19 transcript) relative to vehicle were determined.

The results shown in FIG. 8 indicated that Compound 1 showed PD responses at a tolerated dose via the oral route of administration.

Mouse Pharmacokinetic (PK) Study of Compound 3

Compound 3 was dosed at 5.964 mg/kg IV or 13.307 mg/kg PO to CD-1 mice. Following administration, blood samples were collected at pre-determined time points from five mice via serial bleeding from the tail vein. Blood was collected at 0.083 (0.167 PO only), 0.5, 1, 2, 4, 6, 8, and 24 hours post-dose. The blood samples were centrifuged at 5000 RPM for 5 minutes to collect plasma within 30 minutes of blood collection. After extraction, samples were assayed using LCMS. PK parameters were calculated using non-compartmental analysis in WinNonlin v6.3.

Figure 9:
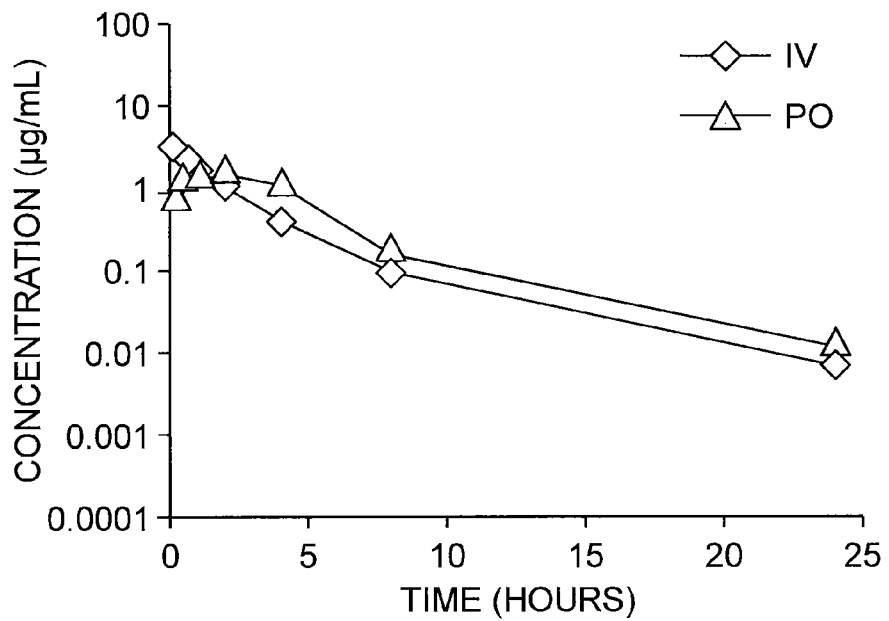
FIG. 9 shows the results of a PK study in CD-1 mice administered Compound 3 at doses of 5.964 mg/kg intravenous (IV) or 13.307 mg/kg oral administration (PO).

The data indicated that Compound 3 showed oral bioavailability and favorable pharmacokinetic properties in the mouse model (FIG. 9, Table 6).

TABLE 6

| Pharmacokinetic Property | Dose | |
|---|---|---|
| | 5.964 mg/kg IV | 13.307 mg/kg PO |
| $C_{max}$ (µg/mL) | NA | 1.567 |
| $t_{max}$ (h) | NA | 2.000 |
| $t_{1/2}$ (h) | 3.660 | 3.322 |
| $AUC_{finite}$ (µg/mL * hr) | 6.210 | 8.136 |
| $AUC_{0-inf}$ (µg/mL * hr) | 6.245 | 8.188 |
| $AUC_{0-inf}/D$ (µg/mL * hr/D) | 1.047 | 0.615 |
| $V_{ss}$ (mL/kg) | 2975.561 | NA |
| $CL_{tot}$ (mL/hr/kg) | 954.975 | NA |
| BA (%) | NA | 58.758 |

Mouse Pharmacokinetic (PK) Study of Compound 4

Compound 4 was dosed at 5 mg/kg IV or 10 mg/kg PO to CD-1 mice. Following administration, blood samples were collected at pre-determined time-points from five mice via serial bleeding from the tail vein. Blood was collected at 0.083 (0.167 PO only), 0.5, 1, 2, 4, 6, 8, and 24 hours post-dose. The blood samples will be centrifuged at 5000 RPM for 5 minutes to collect plasma within 30 minutes of blood collection. After extraction, samples were assayed using LCMS. PK parameters were calculated using non-compartmental analysis in WinNonlin v6.3.

Figure 10:
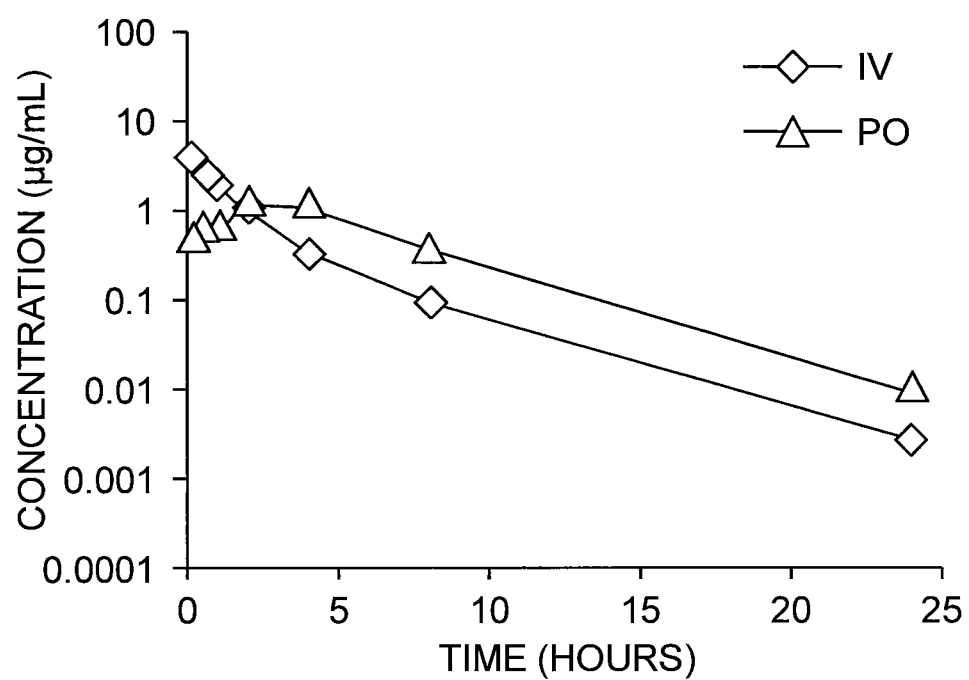
FIG. 10 shows the results of a PK study in CD-1 mice administered Compound 4 at doses of 5 mg/kg intravenous (IV) or 10 mg/kg oral administration (PO).

The data indicated that Compound 4 showed oral bioavailability and favorable pharmacokinetic properties in the mouse model (FIG. 10, Table 7).

TABLE 7

| Pharmacokinetic Property | Dose | |
| --- | --- | --- |
| | 5 mg/kg IV | 10 mg/kg PO |
| $C_{max}$ (μg/mL) | NA | 1.252 |
| $t_{max}$ (h) | NA | 2.000 |
| $t_{1/2}$ (h) | 3.013 | 2.975 |
| $AUC_{0-t}$ (ug/mL * hr) | 6.610 | 7.911 |
| $AUC_{0-inf}$ (ug/mL * hr) | 6.623 | 7.951 |
| $AUC_{0-inf}/D$ (ug/mL * hr/D) | 1.325 | 0.795 |
| $V_{ss}$ (mL/kg) | 1893.683 | NA |
| $CL_{tot}$ (mL/hr/kg) | 754.924 | NA |
| BA (%) | NA | 60.024 |

The results presented above demonstrate that compounds 1, 2, 3 and 4 each possess oral bioavailability and favorable pharmacokinetic properties. This is an improvement over E7107, which has been administered to the patients as intravenous infusion due to its insufficient oral bioavailability (Hong et al. (2014), Invest New Drugs 32, 436-444).

We claim:

1. A compound selected from
a compound of formula 1:

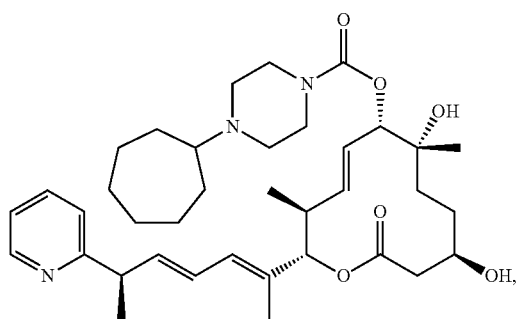

a compound of formula 2:

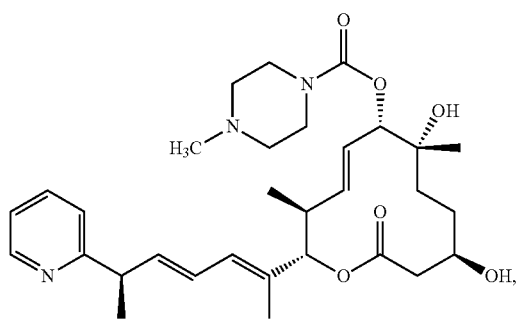

a compound of formula 3:

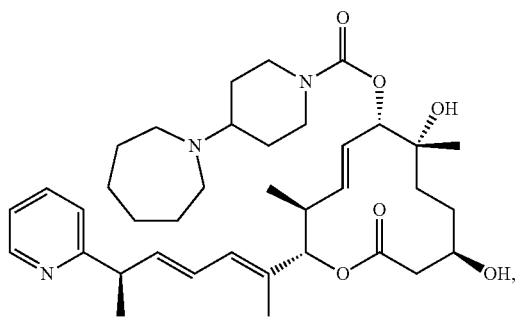

a compound of formula 4:

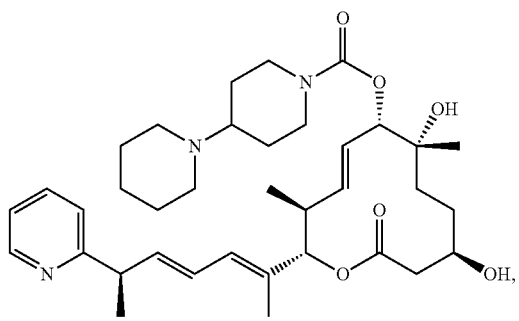

and pharmaceutically acceptable salts thereof.

2. The compound of claim 1 selected from a compound of formula 1:

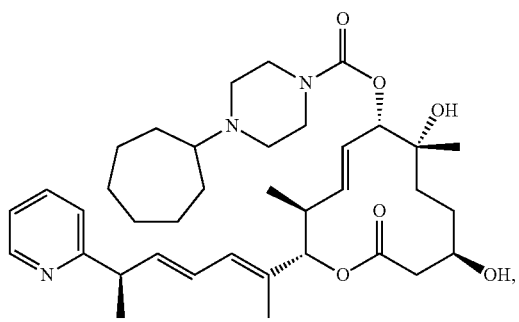

and pharmaceutically acceptable salts thereof.

3. A compound of formula 2:

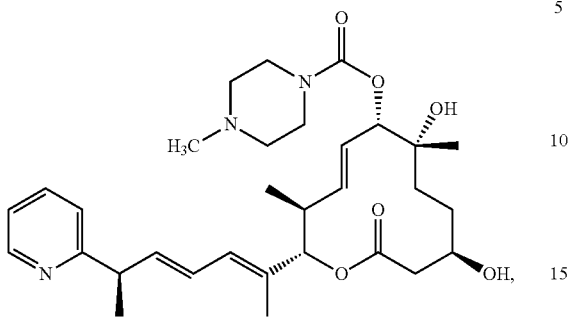

and/or a pharmaceutically acceptable salt thereof.

4. The compound of claim 1 selected from a compound of formula 3:

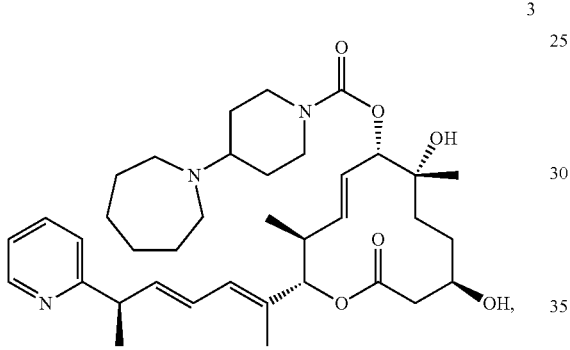

and pharmaceutically acceptable salts thereof.

5. The compound of claim 1 selected from a compound of formula 4:

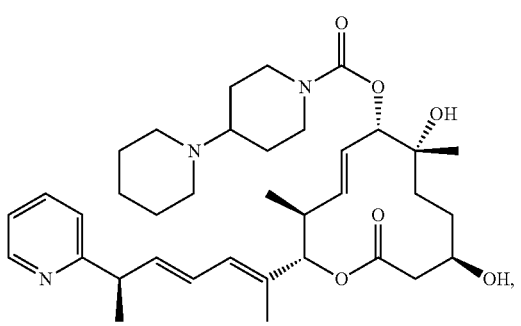

and pharmaceutically acceptable salts thereof.

6. The compound of claim 1, wherein said compound comprises greater than about 80% by weight of one stereoisomer of the compound.

7. A pharmaceutical composition comprising the compound according to claim 1.

8. The pharmaceutical composition of claim 7, wherein said composition is formulated for intravenous, oral, subcutaneous, or intramuscular administration.

9. The pharmaceutical composition of claim 8, wherein said composition is formulated for oral administration.

10. A method of treating cancer in a subject in need thereof, comprising administering to said subject an effective amount of a compound selected from:

a compound of formula 2:

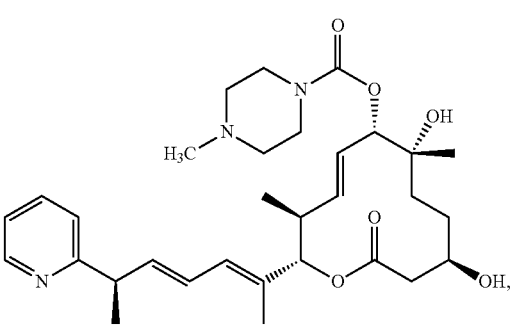

a compound of formula 4:

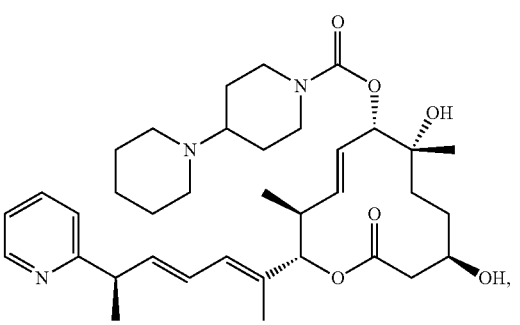

and pharmaceutically acceptable salts thereof, wherein the cancer is selected from myelodysplastic syndrome, chronic lymphocytic leukemia, acute lymphoblastic leukemia, chronic myelomonocytic leukemia, acute myeloid leukemia, colon cancer, pancreatic cancer, endometrial cancer, ovarian cancer, breast cancer, uveal melanoma, gastric cancer, cholangiocarcinoma, and lung cancer wherein said subject has cancer that is positive for one or more mutations in a spliceosome gene or protein selected from Splicing factor 3B subunit 1, U2 small nuclear RNA auxiliary factor 1, Serine/arginine-rich splicing factor 2 and Zinc finger (CCCH) type.

11. The method of claim 10, wherein the cancer is colon cancer.

12. The method of claim 10, wherein the cancer is pancreatic cancer.

13. The method of claim 10, wherein the cancer is acute myeloid leukemia.

14. The method of claim 10, wherein said subject has cancer that is positive for one or more mutations in the splicing factor 3B subunit 1 spliceosome gene or protein.

15. A pharmaceutical composition comprising a compound of formula 2:

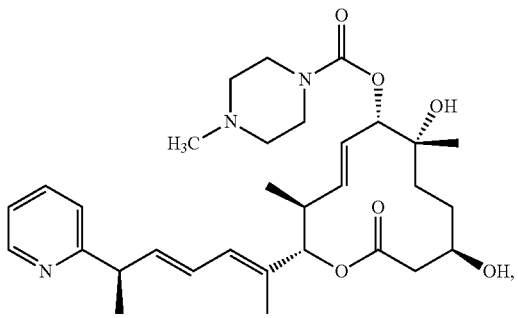

or a pharmaceutically acceptable salt thereof.

16. The pharmaceutical composition of claim 15, wherein said composition is formulated for oral administration.

17. A method of treating cancer in a subject in need thereof, comprising administering to said subject an effective amount of the composition of claim 15, wherein the cancer is selected from myelodysplastic syndrome, chronic lymphocytic leukemia, acute lymphoblastic leukemia, chronic myelomonocytic leukemia, acute myeloid leukemia, colon cancer, pancreatic cancer, endometrial cancer, ovarian cancer, breast cancer, uveal melanoma, gastric cancer, cholangiocarcinoma, and lung cancer wherein said subject has cancer that is positive for one or more mutations in a spliceosome gene or protein selected from Splicing factor 3B subunit 1, U2 small nuclear RNA auxiliary factor 1, Serine/arginine-rich splicing factor 2 and Zinc finger (CCCH) type.

18. The method of claim 17, wherein the cancer is colon cancer.

19. The method of claim 17, wherein the cancer is pancreatic cancer.

20. The method of claim 17, wherein the cancer is acute myeloid leukemia.

21. The method of claim 17, wherein said subject has cancer that is positive for one or more mutations in the splicing factor 3B subunit 1 spliceosome gene or protein.

22. The method of claim 10, wherein the cancer is myelodysplastic syndrome.

23. The method of claim 10, wherein the cancer is chronic lymphocytic leukemia.

24. The method of claim 10, wherein the cancer is acute lymphoblastic leukemia.

25. The method of claim 10, wherein the cancer is chronic myelomonocytic leukemia.

26. The method of claim 10, wherein the cancer is endometrial cancer.

27. The method of claim 10, wherein the cancer is ovarian cancer.

28. The method of claim 10, wherein the cancer is breast cancer.

29. The method of claim 10, wherein the cancer is uveal melanoma.

30. The method of claim 10, wherein the cancer is gastric cancer.

31. The method of claim 10, wherein the cancer is cholangiocarcinoma.

32. The method of claim 10, wherein the cancer is lung cancer.

33. The method of claim 17, wherein the cancer is myelodysplastic syndrome.

34. The method of claim 17, wherein the cancer is chronic lymphocytic leukemia.

35. The method of claim 17, wherein the cancer is acute lymphoblastic leukemia.

36. The method of claim 17, wherein the cancer is chronic myelomonocytic leukemia.

37. The method of claim 17, wherein the cancer is endometrial cancer.

38. The method of claim 17, wherein the cancer is ovarian cancer.

39. The method of claim 17, wherein the cancer is breast cancer.

40. The method of claim 17, wherein the cancer is uveal melanoma.

41. The method of claim 17, wherein the cancer is gastric cancer.

42. The method of claim 17, wherein the cancer is cholangiocarcinoma.

43. The method of claim 17, wherein the cancer is lung cancer.

44. The compound of claim 1, wherein said compound comprises greater than about 90% by weight of one stereoisomer of the compound.

45. The at least one compound of claim 1, wherein said compound comprises greater than about 95% by weight of one stereoisomer of the compound.

46. The compound of claim 1, wherein said compound comprises greater than about 97% by weight of one stereoisomer of the compound.

* * * * *